United States Patent [19]

Kuhla et al.

[11] Patent Number: 4,639,442

[45] Date of Patent: Jan. 27, 1987

[54] BENZOCYCLOBUTENE AMINOALKYLENE ETHERS AND THIOETHERS, PHARMACEUTICAL COMPOSITIONS AND USE

[75] Inventors: Donald E. Kuhla, Doylestown; Henry F. Campbell, Lansdale; William L. Studt, Harleysville, all of Pa.

[73] Assignee: William H. Rorer, Inc., Fort Washington, Pa.

[21] Appl. No.: 798,697

[22] PCT Filed: Apr. 29, 1985

[86] PCT No.: PCT/US85/00789

§ 371 Date: Nov. 1, 1985

§ 102(e) Date: Nov. 1, 1985

[87] PCT Pub. No.: WO85/05032

PCT Pub. Date: Nov. 21, 1985

Related U.S. Application Data

[63] Continuation-in-part of Ser. No. 664,222, Oct. 23, 1984, which is a continuation-in-part of Ser. No. 604,813, Apr. 27, 1984, which is a continuation-in-part of Ser. No. 489,702, Apr. 29, 1983, Pat. No. 4,529,723.

[51] Int. Cl.[4] .................. A61K 31/41; A61K 31/445; C07D 249/14; C07D 401/12

[52] U.S. Cl. .................. 514/212; 546/276; 546/278; 514/222; 546/279; 548/200; 514/228; 548/265; 548/266; 514/230; 548/267; 514/232; 514/234; 514/236; 514/237; 514/314; 514/318; 514/323; 514/326; 514/340; 514/341; 514/343; 514/365; 514/383; 514/384; 544/58.5; 544/58.7; 544/60; 544/62; 544/79; 544/128; 544/131; 544/132; 544/133; 546/167; 546/187; 546/194; 546/201; 546/209; 546/210; 540/525; 540/544; 540/603; 540/553

[58] Field of Search .............. 544/58.5, 58.7, 60, 544/62, 128, 131, 132, 133, 79; 546/167, 144, 201, 209, 210, 276, 278, 279, 187; 548/200, 265, 267, 266; 260/244.4, 245.5; 514/212, 222, 228, 230, 232, 234, 236, 237, 314, 318, 323, 326, 340, 341, 343, 365, 383, 384

[56] References Cited

U.S. PATENT DOCUMENTS 3,308,157 3/1967 Robertson et al. .................. 544/106
4,410,523 10/1980 Ollis et al. .......................... 548/267

*Primary Examiner*—Robert W. Ramsuer
*Attorney, Agent, or Firm*—James A. Nicholson; Alexis Barron; Martin F. Savitzky

[57] ABSTRACT

A class of benzocyclobutene aminoalkylene ether and thioether compounds exhibiting pharmacological activity, including anti-secretory and anti-ulcerogenic activity, pharmaceutical compositions comprising these compounds, and methods for the treatment of gastrointestinal hyperacidity and ulcerogenic disorders in mammals using said compositions.

22 Claims, No Drawings

BENZOCYCLOBUTENE AMINOALKYLENE ETHERS AND THIOETHERS, PHARMACEUTICAL COMPOSITIONS AND USE

This is a continuation-in-part of U.S. application Ser. No. 664,222, filed Oct. 23, 1984, which is a continuation-in-part of U.S. application Ser. No. 604,813, filed Apr. 27, 1984, which is a continuation-in-part of U.S. application Ser. No. 489,702, filed Apr. 29, 1983 now U.S. Pat. No. 4,529,723.

FIELD OF THE INVENTION

This invention relates to a class of benzocyclobutene compounds characterized by an ether or thioether substituent on the phenyl ring and an exocyclic nitrogen substituent on the cyclobutene ring of the bicyclic ring system and methods for the treatment of physiological disorders, including gastrointestinal disorders in humans and other mammals.

REPORTED DEVELOPMENTS

Gastrointestinal hyperacid secretion, stomach and intestinal ulceration, and gastritis are major gastrointestinal disorders observed in the general adult populations of industrialized societies. Many factors, including the production of excess gastric acid and the weakening of the lining of the stomach and gastrointestinal tract against such acid are implicated as causes of these disorders. Traditional treatment of these disorders has involved the administration of antacids to neutralize the excess gastric acid and the administration of antisecretory drugs which generally reduce the production of all gastric secretions.

In the last few years, the treatment of gastrointestinal disorders such as peptic ulcer has changed to include the use of anti-secretory drugs which selectively block the production of gastric acid. These drugs are believed to interfere with the body's physiological pathway responsible for the production of gastric acid by blocking the action of histamine. Histamine production is induced in the body by a number of stimuli, including stress, allergic reaction, etc., and acts to increase gastric secretion, dilate blood vessels and stimulate smooth muscle tissue. Histamine is believed to function by way of interaction with histamine receptors in the body. The subdivision of these receptors into two groups, the $H_1$- and $H_2$-receptors, was proposed by Ash and Schild (Brit. J. Pharmacol. Chemother, 1966, 27, 427) and Black et al (Nature 1972, 236, 385). The $H_1$-receptor is involved in the bronchial and gastrointestinal smooth muscle stimulative action of histamine. Drugs which block this action are labelled "antihistamines" (e.g. mepyramine).

Black et al, cited above, described the group of substances which act as histamine receptors other than the $H_1$-receptor as the $H_2$-receptors. Blocking the action of histamine at the $H_2$-receptors will selectively block histamine's stimulative action on gastric acid secretion and heart rate. Burimamide was the first clinically effective $H_2$-receptor antagonist inhibiting gastric secretion in man; but Burimamide's oral absorptivity is poor. Subsequent studies developed the orally active Metiamide, the side effects of which limited clinical use, and Cimetidine which has been marketed as an anti-ulcer drug. A number of classes of heterocyclic chemical compounds have been reported as $H_2$-receptor antagonists, for example, those disclosed in U.S. Pat. Nos. 4,104,381, 4,279,819, 4,323,566, 4,390,701, 4,395,553, and British published patent applications GB No. 2067987A and GB No. 2047238A, and EPO publication No. 0081955A2, the disclosures of which are incorporated by reference.

Another method for the prevention or treatment of gastric ulcer comprises the use of drugs which neither neutralize nor inhibit the secretion of gastric acid. These drugs constitute a class of anti-ulcer compounds which function to enhance the normal defense mechanisms of the body, rather than to reduce normal body secretions, and are described as "cytoprotective" agents. It has been proposed that such agents act to strengthen the mucosal lining of the gastrointestinal system by one or more mechanisms, thereby preventing any damage which could result from the action of strong gastric acid. Prostaglandins have been implicated in the mechanism of cytoprotection by a number of workers in the field. See, the discussion of cytoprotection in Robert, Andre, "Prostaglandins and Digestive Diseases", *Advances in Prostaglandin and Thromboxane Research*, Vol. 8 (Raven Press, N.Y. 1980), and Robert et al, "Cytoprotection by Prostaglandins in Rats", *Gastroenterology*, 77, 433–443 (1979), hereby incorporated by reference. Drugs, other than prostaglandins, which exhibit cytoprotective activity include carbenoxolone sodium, reported to exhibit undesirable side effects, such as edema, diastolic hypertension or hypokalemia, and the thiazol-2-yl-carbamoylcarboxylic acids, esters and imides described in U.S. Pat. No. 4,321,372.

Compounds of the present invention comprise benzocyclobutenes which exhibit anti-secretory activity, $H_2$-receptor antagonist activity, anti-ulcer activity and cytoprotective activity.

SUMMARY OF THE INVENTION

This invention comprises a class of compounds according to Formula I

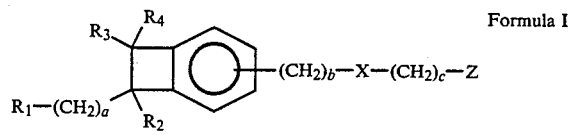

wherein:
a is 1 or 2;
b is 0 or 1;
c is 2, 3 or 4;
X is oxygen, sulfur,

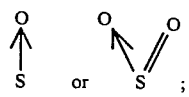

Z is —NHR$_7$,

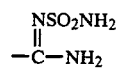

or —CN;
R$_1$ is —NR$_5$R$_6$, or $$\begin{array}{c} NR_9 \\ \| \\ -C-NR_5R_6; \end{array}$$

$R_2$, $R_3$ and $R_4$ are each independently hydrogen, lower alkyl, allyl, arylloweralkyl or loweralkoxycarbonyl, or lower alkyl substituted by hydroxy, loweralkoxycarbonyl or $-NR_5R_6$;

$R_5$ and $R_6$ are each independently H or alkyl, or both together with the nitrogen to which they are attached form a 5, 6 or 7-membered ring which may include one to three additional hetero atoms of N, O or S;

$R_7$ is selected from the group consisting of H, $$\begin{array}{ccc} N-CN & CH-NO_2 & N-CN \\ \| & \| & \| \\ -C-NH-R_8, & -C-NH-R_8, & -C-S-R_8, \end{array}$$

[structures with S, N rings bearing NH-R_8, and a benzene ring with R_16 and N-R_17 substituents]

[structure with SO_2, N, S ring with NHR_8, and a cyclobutenedione structure with NHR_8]

[structure with SO_2, N, S ring with NHR_8, and pyrazole-like structure with R_8, N-N, R_10]

[structure showing pyrimidinone with alkaryl substituent and NH]

$R_8$ is H or lower alkyl;

$R_9$ is H or lower alkyl or $R_9$ together with $R_5$ are ethylene or propylene and form a 5 or 6 membered ring with the nitrogen atoms to which they are attached;

$R_{10}$ is hydrogen, lower alkyl, lower alkenyl, aryl, arloweralkyl, hydroxyloweralkyl, acyloxyloweralkyl, loweralkoxyloweralkyl, aryloxyalkyl, aroyloxyalkyl, aralkyloxyalkyl, aminoalkyl, alkylaminoalkyl, dialkylaminoalkyl, hydroxy, alkoxy, alkylthio, halogen or $NR_{11}R_{12}$, where:

$R_{11}$ is hydrogen, lower alkyl, lower alkenyl or arloweralkyl; and $R_{12}$ is hydrogen, $COR_{13}$, $SO_2R_{14}$ or $$\begin{array}{c} X \\ \| \\ C-NHR_{15}; \end{array}$$

$R_{13}$ is hydrogen, lower alkyl, aryl, arloweralkyl, loweralkoxy, heteroaryl, or monocyclic heteroarylalkyl;

$R_{14}$ is lower alkyl or aryl;

$R_{15}$ is hydrogen, lower alkyl, cycloloweralkyl, aryl or lower aralkyl;

$R_{16}$ is halo, amino, nitro, cyano, hydroxy, lower alkyl, lower alkoxy, lower alkanoyl, cycloloweralkyl, mono- or di-lower alkyl amino, lower alkanoyl, lower alkanoyl amino, haloloweralkyl, aryl, mercapto, loweralkoxy carbonyl, carboxy, loweralkylthio, loweralkylsulfonyl, sulfamoyl, or lower alkyl sulfamoyl; and $R_{17}$ is $SO_2$, SO, S or $C=O$;

or a pharmaceutically acceptable salt thereof.

Compounds within the scope of Formula I exhibit physiological activity in mammals including anti-secretory activity, histamine $H_2$-receptor antagonist activity, anti-ulcer activity and cytoprotective activity.

Another aspect of this invention relates to the class of geometric isomeric compounds according to Formula I, which class of compounds exhibits an unexpected and surprising level of physiological activity including anti-secretory, histamine $H_2$-receptor antagonist and anti-ulcer activity.

This invention also relates to methods for the treatment and prevention of gastrointestinal hyperacidity and ulcerogenic disorders in humans and other mammals comprising administering to a patient an effective amount of a compound within the description of Formula I.

DETAILED DESCRIPTION OF THE INVENTION

Preferred classes of compounds according to this invention are described by Formulae II, III and IV below.

[Formula II: bicyclic structure with R_2, R_3, R_4 substituents, CH_2-NR_5R_6 and $(CH_2)_b-X-(CH_2)_c-Z$]

Formula II

[Formula III: bicyclic structure with R_2, R_3, R_4, CH_2-N(R_5)(R_6) and $(CH_2)_b-X-(CH_2)_c-Z$]

Formula III

[Formula IV: bicyclic structure with R_2, R_3, R_4, $(CH_2)_n$, N-CH_2 and $O-(CH_2)_c-NHR_7$]

Formula IV wherein:

n is 4, 5 or 6; and b, c, X, Z, and $R_1$ through $R_{17}$ are as described above.

A most preferred class of compounds within the scope of Formula I comprises the compounds of Formula I wherein: a is 1.

A preferred subclass of compounds is described by Formulae I, II, III or IV, wherein:

a is 1;

b is 0;

X is oxygen;

Z is NHR₇; and at least one of R₂, R₃ and R₄ is hydrogen.

A special embodiment of this subclass are compounds of Formulae I, II, III or IV, wherein:

R₂, R₃ and R₄ are hydrogen; or

R₂ and R₃ are hydrogen; or

R₂ is hydrogen; or

R₃ and R₄ are hydrogen.

A preferred Z substituent is selected from the group including

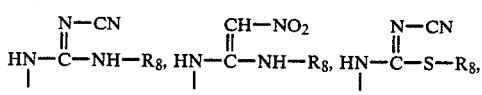

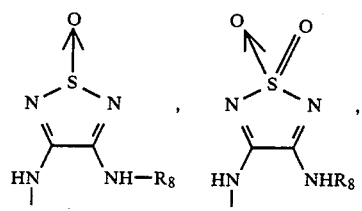

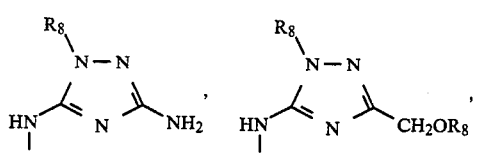

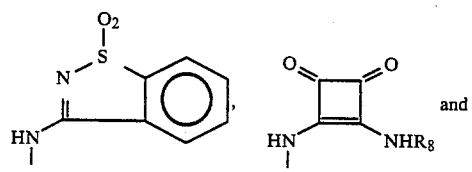

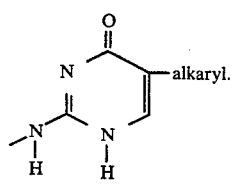

A most preferred subclass of compounds is described by Formula II, III or IV, wherein: Z is

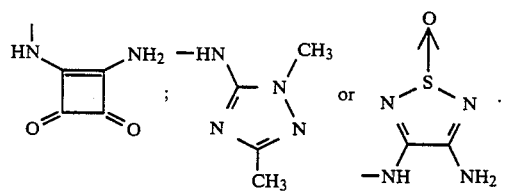

A most preferred class of compounds is described by Formula V.

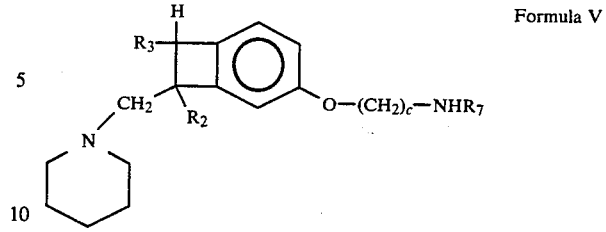

Formula V wherein:

c is 2, 3 or 4;

R₂ and R₃ are hydrogen, loweralkyl, allyl or diloweralkylaminomethane, provided that one of R₂ and R₃ is hydrogen; or a pharmaceutically acceptable salt thereof.

A particularly interesting class of compounds according to Formula V comprises those compounds wherein R₇ is 4-(3-amino-1,2,5-thiadiazole-1-oxide), 5-(3-amino-1-methyl-1H-1,2,4-triazole) or 1-(2-amino-1-cyclobutene-3,4-dione).

The compounds of Formulae I to V may also form hydrates and exhibit tautomerism. Formulae I to V are intended to encompass all hydrates and tautomers, as well as any diastereomers and optical enantiomers.

As employed above and throughout the disclosure, the following terms, unless otherwise indicated, shall be understood to have the following meanings:

"Lower alkyl" means an alkyl group as above, having 1 to about 4 carbon atoms. Examples of lower alkyl groups are methyl, ethyl, n-propyl, isopropyl, butyl, sec-butyl, and tert-butyl.

"5, 6 or 7 membered ring" means a ring of the formula

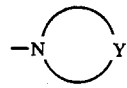

where Y is alkylene or alkylidenyl having from one to six carbon atoms, and may include one to three atoms of N, O or S. Exemplary heterocyclic groups include piperidinyl, pyrrolidinyl, morpholinyl, azepinyl, pyrrolyl, imidazolyl, pyrazolyl, and thiamorpholinyl.

"Aroyl" means an acyl derivative of an aromatic carboxylic acid such as benzoyl and quinolyl.

"Heteroaryl" means a five or six membered monocyclic ring or 9 or 10 membered bicyclic ring either of which may contain one or more heteroatoms of nitrogen, oxygen or sulfur, including furyl, pyridyl, thiazolyl, quinolinyl, indolyl or thienyl.

"Lower alkanoyl" means an acyl derivative of a lower alkanoic acid such as acetyl and propionyl.

"Aryl" means an aromatic hydrocarbon radical group such as phenyl, toluyl, quinolyl, pyridyl, and includes phenyl, toluyl, quinolyl or pyridyl substituted by one or more substituent groups including lower alkyl, halo, carboxyl, amino, loweralkyl amino, amido, hydroxyl, nitro, cyano, or sulfonyl. Preferred aryl groups include phenyl and toluyl.

Representative examples of compounds of this invention are listed below in Table A.

TABLE A

[Structure: bicyclic aromatic with CH₂-N-piperidine-like ring (CH₂)d and O-(CH₂)c-NH-R₆ substituent]

| d | c | R₆ |
|---|---|---|
| 0 | 3 | 1-methyl-1,2,4-triazole with NHC(O)CH₃ |
| 0 | 3 | 1-methyl-1,2,4-triazole with CH₂OCH₃ |
| 0 | 3 | 1-methyl-1,2,4-triazole with CH₂-O-C(O)CH₃ |
| 0 | 3 | cyclobutenedione with NHCH₃ |
| 0 | 3 | cyclobutenedione with NH-C(O)CH₃ |
| 1 | 3 | 1-methyl-1,2,4-triazole with CH₂OH |
| 1 | 3 | 1-methyl-1,2,4-triazole with CH₂OCH₃ |
| 1 | 3 | 1-methyl-1,2,4-triazole with CH₂-O-C(O)CH₃ |
| 1 | 3 | 1-methyl-1,2,4-triazole with NH₂ |
| 1 | 3 | 1-methyl-1,2,4-triazole with NHCH₃ |

TABLE A-continued

| d | c | R₆ |
|---|---|---|
| 1 | 3 | cyclobutenedione with NHCH₃ |
| 1 | 3 | cyclobutenedione with NH₂ |
| 1 | 3 | cyclobutenedione with NHC(O)CH₃ |
| 1 | 3 | benzisothiazole S,S-dioxide |
| 0 | 4 | 1-methyl-1,2,4-triazole with NHC(O)CH₃ |
| 0 | 4 | 1-methyl-1,2,4-triazole with CH₂OCH₃ |
| 0 | 4 | 1-methyl-1,2,4-triazole with CH₂-O-C(O)CH₃ |
| 0 | 4 | cyclobutenedione with NHCH₃ |
| 0 | 4 | cyclobutenedione with NH-C(O)CH₃ |
| 1 | 4 | 1-methyl-1,2,4-triazole with CH₂OH |
| 1 | 4 | 1-methyl-1,2,4-triazole with CH₂OCH₃ |

TABLE A-continued
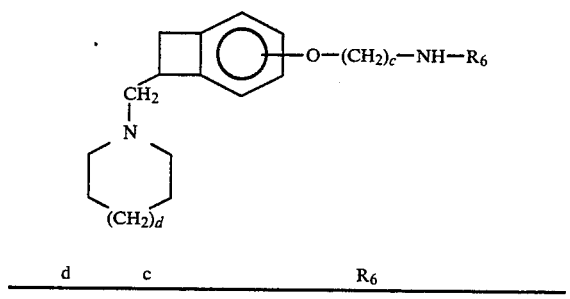
| d | c | R6 |
|---|---|---|
| 1 | 4 | 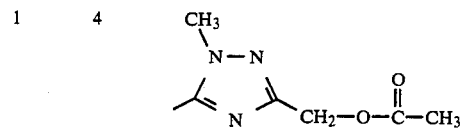 |
| 1 | 4 | 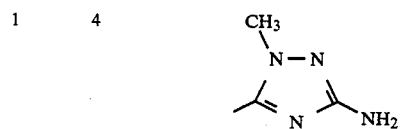 |
| 1 | 4 | 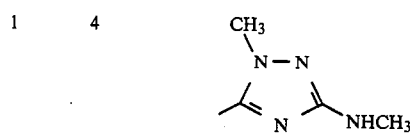 |
| 1 | 4 | 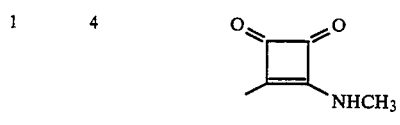 |
| 1 | 4 |  |
| 1 | 4 | 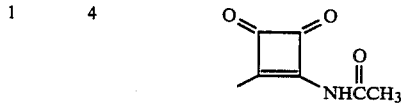 |
| 1 | 4 | 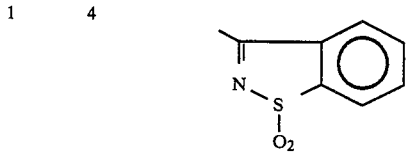 |
| 0 | 3 | 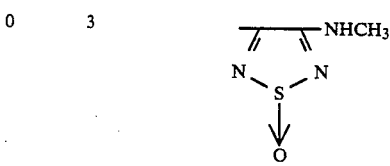 |
| 0 | 3 | 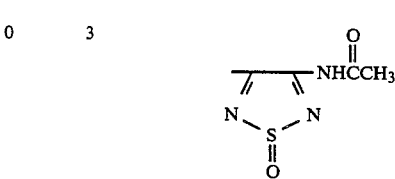 |
TABLE A-continued
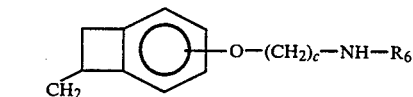
| d | c | R6 |
|---|---|---|
| 0 | 4 | 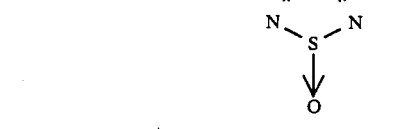 |
| 0 | 4 | 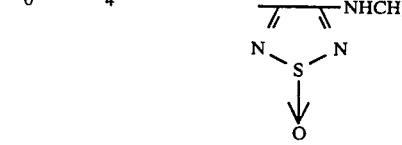 |
| 0 | 4 | 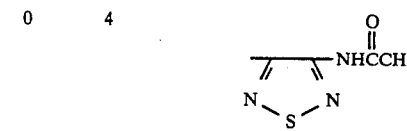 |
| 1 | 3 |  |
| 1 | 3 | 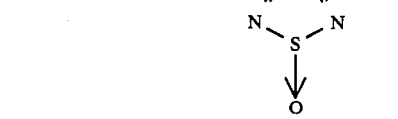 |
| 1 | 3 | 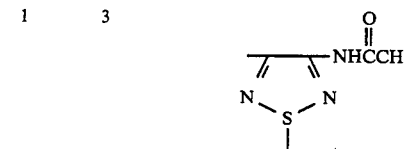 |
| 1 | 4 |  |
| 1 | 4 | 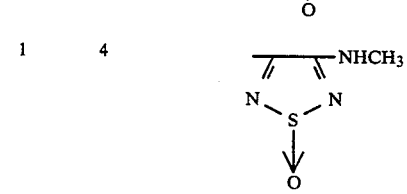 |

TABLE A-continued

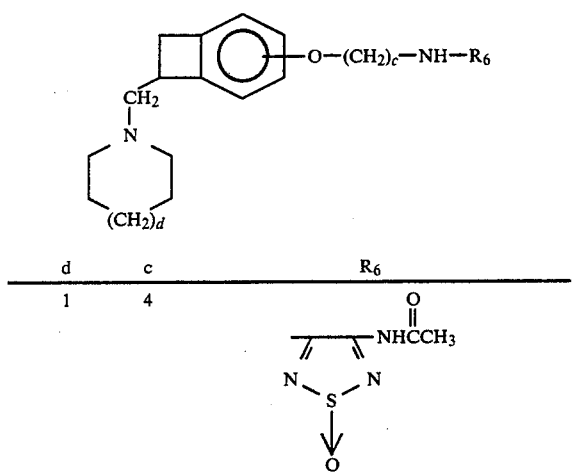

| d | c | R₆ |
|---|---|---|
| 1 | 4 | (thiadiazole-NHC(O)CH₃ group) |

Compounds within the scope of Formula I are referred to as benzocyclobutenes and may be prepared according to the following reaction sequences.

3-Substituted benzocyclobutenes may be prepared starting from a 4-substituted indanone by means of a ring contraction reaction effected by photolysis of the appropriately substituted diazoindanone. The ring contraction reaction produces a 1-carboxylic acid benzocyclobutene which may be converted to the corresponding 1-aminomethylene compound by reduction to the alcohol followed by the formation and displacement of an appropriate leaving group by the desired nucleophilic amine. Scheme I below depicts an exemplary reaction sequence.

Scheme I

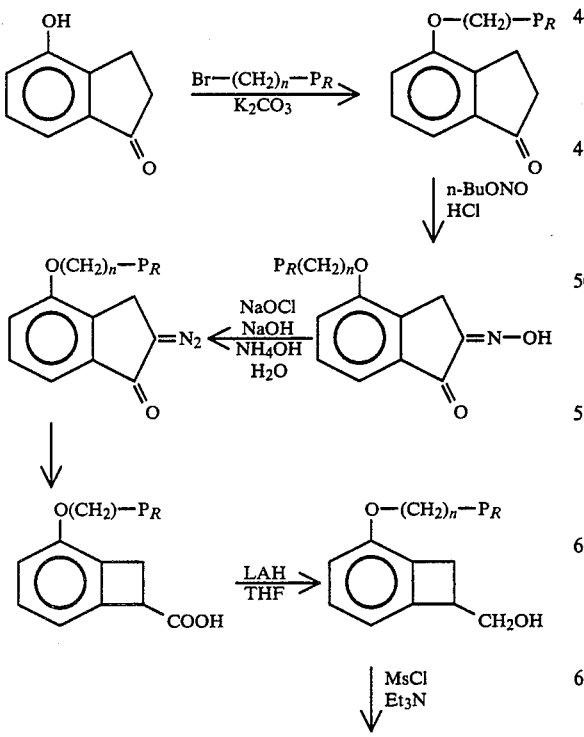

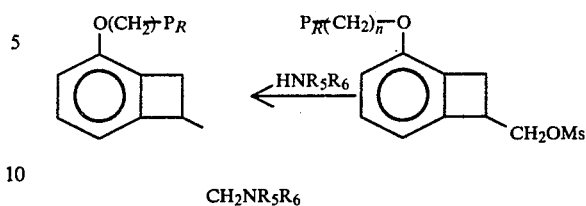

The $P_R$ group designated in Scheme I may be any protecting group which can be subsequently converted into an amino group by means known to persons skilled in the art.

Another pathway to the 1-aminomethylene-3-aminoalkoxy-benzocyclobutenes of Formula I involves the 1-amido intermediate shown in Scheme II below. The amide can be used to prepare the 1,1-disubstituted benzocyclobutenes, such as, the 1-methyl-1-(1-piperidinylmethyl) benzocyclobutenes. The benzocyclobutenecarbon atom alpha to the amido functionality may be alkylated, acylated, benzylated or allylated with the appropriate reagent. The alkylation (or acylation) may be conducted under standard conditions using a strong base such as diisopropylamine anion and an appropriate electrophilic reagent.

Scheme II

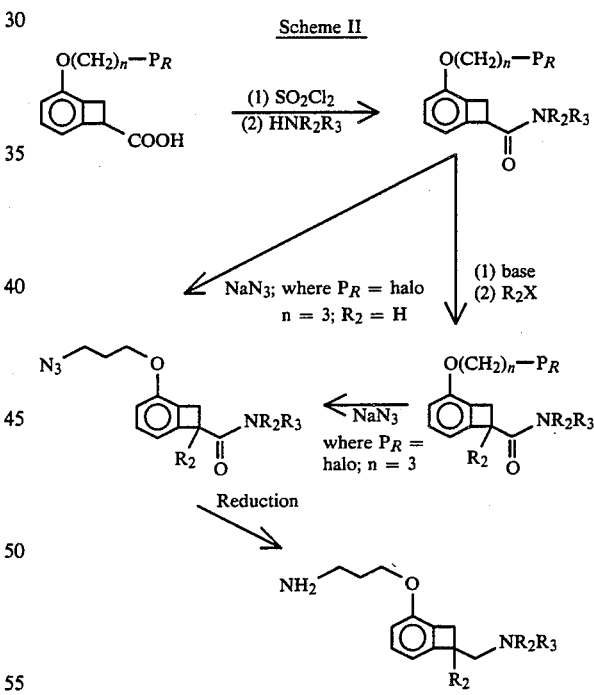

Another advantage of the amide intermediate is the ability to reduce the amide and the azide functionality in one step with a hydride reducing agent such as lithium aluminum hydride, as shown in Scheme II above.

It should be noted that when n is zero and Pr is methyl in Scheme II above, the methyl group can be removed and the resulting hydroxy compound reacted with a dihaloalkyl reagent under basic conditions. The azido functionality can then be formed and reduced to the amine as shown above.

5-substituted benzocyclobutenes may be prepared starting from a para-alkoxy benzaldehyde which may be condensed with acetonitrile (or cyanoacetic acid), followed by hydrogenation, (decarboxylation if cyanoacetic acid is the condensing agent) and bromination to yield 1-cyano-2-(4-alkoxy-3-bromo-phenyl)ethane. The bromo compound is cyclized to the 1-cyanobenzocyclobutene, hydrolyzed to the carboxylic acid derivative and converted to the 1-aminomethylene benzocyclobutene by reactions described herein above. Scheme III below depicts an exemplary reaction sequence.

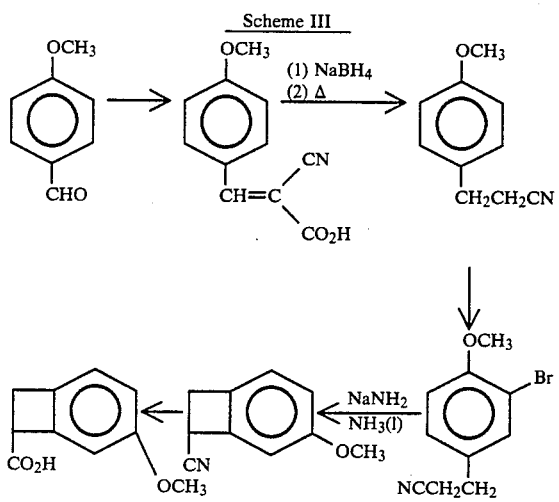

The 5-methoxy intermediates shown in Scheme III above, may be converted into the 1-amido compound by treating the carboxylic acid intermediate with thionyl chloride and an amine of the formula $HNR_5R_6$. The resulting amide may be alkylated or carried on to the next step unalkylated. Demethylation of the 5-methoxy group and phenolic alkoxylation with a dihalo lower alkyl compound, such as 1,3-dibrompropane, results in the 5-(3-haloalkoxy) benzocyclobutene intermediate. The 5-(3-aminoalkoxy) benzocyclobutene intermediate is formed by treatment with sodium azide followed by hydride reduction.

The following modification of the synthetic sequence of Scheme III above provides an intermediate having substitutents in the 2-position of the benzocyclobutene ring. Condensation of a paramethoxyphenyl, $R_3$-ketone with an acetonitrile derivative such as dialkylcyanomethylphosphonate results in an $\alpha,\beta$-unsaturated cyano compound. The unsaturated intermediate can undergo a 1,4-addition to form the 2,2-disubstituted intermediate or it can be hydrogenated to form the 2-substituted intermediate. Bromination and cyclization results in the 1-cyano-2-$R_3$-benzocyclobutene compounds. An exemplary reaction sequence is depicted in Scheme IV below.

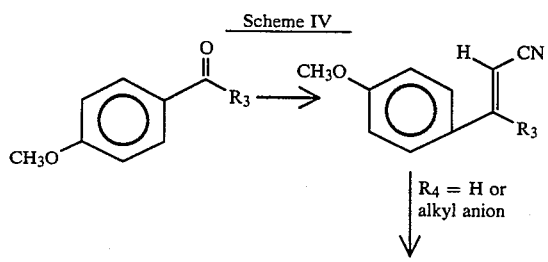

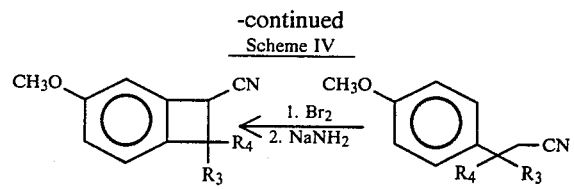

The 2,2-disubstituted benzocyclobutene compound shown in Scheme IV above can be utilized in the reaction sequences described above to afford the corresponding 1-aminomethylene-2,2-disubstituted compounds of Formula I.

The addition of the terminal $R_7$ group (where $R_7$ is other than H) comprises treating the 3-aminoalkoxy compounds with an $R_7$ end group precursor unit including those groups listed in Scheme V. The preparation of the precursors of the $R_7$ groups and the reaction conditions under which they are coupled to the primary amine are fully described in U.S. Pat. Nos. 4,104,381, 4,279,819, 4,323,566, 4,390,701, 4,395,553, and GB No. 2047238A, GB No. 2067987A, and EPO Publication No. 0081955A2, hereby incorporated by reference.

Compounds within Formula I which include the $R_4$ group

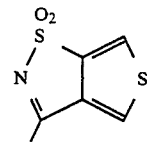

may be prepared from the methyl mercaptyl derivative formed from the oxo-precursor, which is described in the *Journal of Organic Chemistry*, Vol. 45, 617 (1980), hereby incorporated by reference. Upon treatment of the oxo-precursor with $P_2S_5$ in pyridine, the thione analog is formed, which in turn forms the methyl mercaptan compound on treatment with base and methyl iodide.

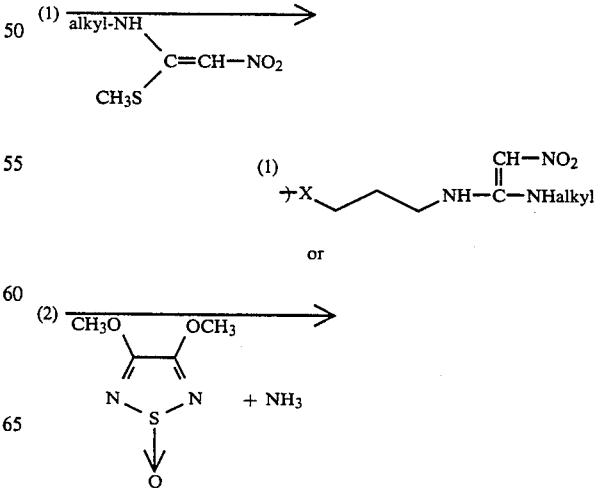

-continued
Scheme V

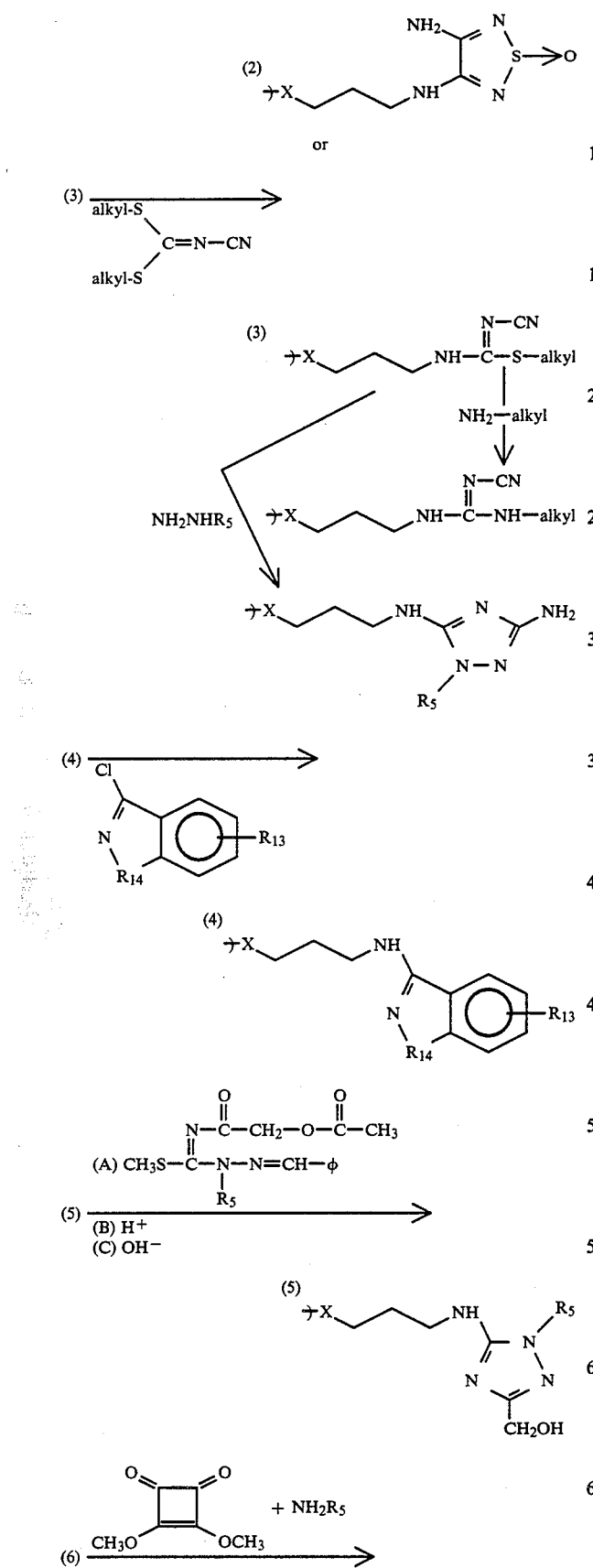

-continued
Scheme V

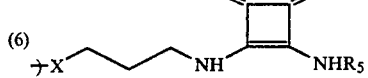

When Z in Formula I is CN or sulfamoyl amidine, the reaction sequence is slightly modified as shown below in Scheme VI. Reaction of the phenolic intermediate with a cyano-substituted alkylating agent such a 3-cyanopropylchloride in the presence of a base produces the cyano ether compound. Reduction of the cyano group with a hydride such a lithium aluminum hydride results in the amino compound. Treatment of the cyano compound with anhydrous methanolic HCl yields an imidate intermediate which is converted to the sulfonyl amidine by treatment with sulfamide in methanol. For a complete discussion of this preparatory sequence, see U.S. Pat. No. 4,283,408, incorporated herein by reference.

Scheme VI

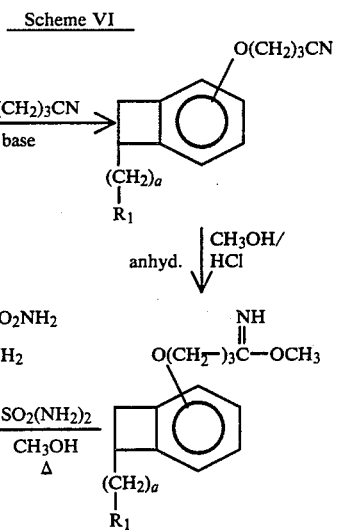

The analogous thioether compounds may be prepared by reacting a cyano mercaptan with the appropriate halomethylene intermediate as shown in Scheme VII below. The amino sulfonyl amidine compound is prepared by reaction sequences similar to those described above.

Scheme VII

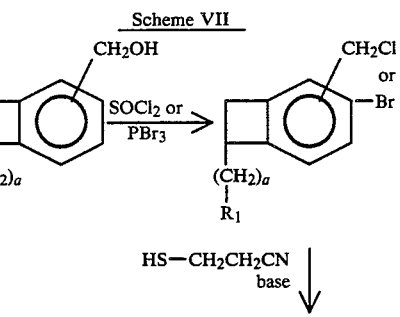

-continued
Scheme VII

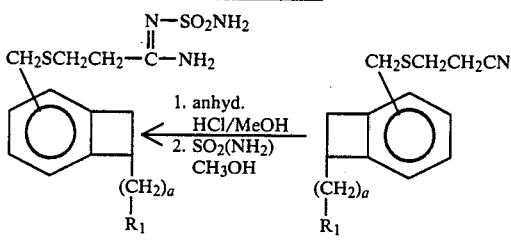

The compounds of this invention may be readily converted to their non-toxic acid addition salts by customary methods in the art. The non-toxic salts of this invention are those salts the acid components of which is pharmacologically acceptable in the intended dosages, including those prepared from inorganic acids such as hydrochloric acid, hydrobromic acid, sulfuric acid, nitric acid and phosphoric acid, and from organic acids such a methane sulfonic acid, benzenesulfonic acid, acetic acid, propionic acid, malic acid, oxalic acid, succinic acid, glycolic acid, lactic acid, salicyclic acid, benzoic acid, nicotinic acid, phtalic acid, stearic acid, oleic acid, abietic acid, etc.

The following are selected examples of the preparation of the compounds to this invention.

EXAMPLE 1

The Preparation of 5-(3-Aminopropoxy)-1-(1-Piperidinylmethyl)Benzocyclobutene

Step 1. α-Cyano-4-methoxycinnamic acid

A stirred mixture of p-anisaldehyde (60.7 ml), ammonium acetate (7.5 g), cyanoacetic acid (42.5 g), pyridone (70 ml) in toluene (390 ml) is refluxed using a Dean Stark trap until about 9 ml of water is collected. The reaction mixture is cooled and the solid precipitate filtered and stirred with 10% aqueous HCL. The solid is filtered and recrystallized from methanol yielding the desired product.

Step 2. α-Cyano-β-(4-methoxyphenyl)propionic acid

Sodium borohydride (30.2 g) is added portionwise over a period of 2 hours to a stirred mixture of α-cyano-4-methoxycinnamic acid (52.5 g) in aqueous saturated NaHCO$_3$ (200 ml) and methanol (600 ml) cooled to about 15° C. The reaction mixture is allowed to warm to RT, stirred at RT for 30 min and concentrated in vacuo. The residue is partitioned between water and ether and the aqueous layer acidified and extracted with ether. The ether extract is washed, dried over Na$_2$SO$_4$, filtered and the filtrate evaporated in vacuo producing a liquid which is crystallized from toluene yielding the desired product as a solid, M.P. 94°–95° C.

Step 3. 4-Methoxyphenylpropionitrile

A stirred solution of α-cyano-β-(4-methoxyphenyl)-propionic acid (127.3 g) in DMF (280 ml) is heated to 150° C. for 5 hours. The reaction mixture is cooled, poured into a liter of water and extracted with ether. The ether extract is washed, dried over Na$_2$SO$_4$, filtered and the filtrate evaporated in vacuo yielding a liquid which upon distillation yields the decarboxylated product as a clear liquid, B.P. 115° C. (1 mm).

Step 4. 3-Bromo-4-methoxyphenylpropionitrile

Bromine (21.4 ml) is added dropwise over a period of 1 hour to a stirred solution of 4-methoxyphenylpropionitrile (67.5 g) and sodium acetate (68.4 g) in glacial acetic acid (420 ml). The reaction mixture is stirred for an additional 30 minutes and partitioned between water and ether. The ether layer is washed with sodium carbonate solution, 10% aqueous NaOH, saturated salt, dried over Na$_2$SO$_4$ and filtered. The filtrate is evaporated in vacuo yielding the desired product, B.P. 155°–158° C. (4 mm).

Step 5. 1-Cyano-5-methoxybenzocyclobutene

3-Bromo-4-methoxyphenylpropionitrile (54.28 g) is added dropwise over a period of about 20 minutes to a stirred suspension of sodium amide (37.1 g) in liquid ammonia (250 ml) cooled to about −33° C. under nitrogen. The reaction mixture is refluxed for 3 hours after which ammonium nitrate (54.3 g) is added slowly to the mixture. The ammonia is allowed to evaporate overnight and the residue partitioned between water and methylene chloride. The organic fraction is washed with 5% HCl, saturated NaCl, dried over Na$_2$SO$_4$, filtered and the filtrate evaporated in vacuo yielding a liquid which is chromatographed (silica gel; 300 g; Hex-/Ethyl Acetate 3:1) affording the desired product as a clear liquid.

Step 6. 5-Methoxybenzocyclobutene-1-carboxylic acid

1-Cyano-5-methoxybenzocyclobutene (29 g) is stirred with saturated KOH in ethanol (180 ml) for about 12 hours under nitrogen at RT. Water (60 ml) is added to the reaction mixture which is refluxed for about 3 hours. The mixture is cooled to RT, diluted with water, washed with ether and the aqueous layer acidified forming an oil. The oil is dissolved in ether and the ethereal solution washed, dried over Na$_2$SO$_4$, filtered and evaporated in vacuo affording the desired product as an oil.

Step 7. 5-Methoxy-1-hydroxymethylbenzocyclobutene

A solution of 5-methoxybenzocyclobutene-1-carboxylic acid (32.0 g) in ether (1.2 l) is added dropwise to a stirred suspension of LAH (15.5 g) in ether (650 ml) under nitrogen. The reaction mixture is stirred at RT for 4 hours, after which, water (15.5 ml), 15% NaOH (15.5 ml) and a second portion of water added (46 ml) sequentially to the reaction mixture resulting in the formation of a precipitate. The ethereal layer is filtered, dried over Na$_2$SO$_4$, filtered and concentrated in vacuo yielding the desired product as an oil.

Step 8. 5-Methoxy-1-hydroxymethylbenzocyclobutene mesylate

Methane sulphonyl chloride (13.4 ml) is added dropwise to a stirred solution of 5-methoxy-1-hydroxymethyl benzocyclobutene (26 g) and triethylamine (26.5 ml) in methylene chloride (670 ml) cooled to 0° C. under nitrogen. The reaction mixture is allowed to warm to RT, stirred for 2 hours at RT, washed with water and saturated salt, dried over Na$_2$SO$_4$, and filtered. The filtrate is concentrated in vacuo yielding the desired product as a liquid.

Step 9.
5-Methoxy-1-(1-piperidinylmethyl)-benzocyclobutene

A solution of 5-methoxy-1-hydroxymethylbenzocyclobutene mesylate (38 g) and piperidine (45 ml) in toluene (180 ml) is refluxed under nitrogen for about 12 hours. The reaction mixture is filtered and the filtrate is evaporated in vacuo leaving a liquid residue which is used without further purification in the next step.

Step 10.
5-Hydroxy-1-(1-piperidinylmethyl)-benzocyclobutene

A solution of 5-methoxy-1-(1-piperidinylmethyl)benzocyclobutene (0.75 g), trimethylsilyliodide (0.6 ml) in chloroform (1.6 ml) is stirred for about 18 hours under nitrogen at about 50° C.

Methanol is added to the reaction mixture resulting in the formation of a precipitate which is filtered and the filtrate concentrated in vacuo to a red oil. The oil is partitioned between ether and saturated aqueous sodium bicarbonate. The layers are separated and the aqueous layer washed with ether. The ether extracts are combined, washed with saturated salt, dried over Na$_2$SO$_4$, filtered and the filtrate evaporated affording the desired phenolic compound as a solid.

Step 11.
5-(3-Bromopropoxy)-1-(1-piperidinylmethyl)benzocyclobutene

Potassium hydroxide (1.5 g, 10%) is added over a period of 1 hour 15 min to a stirred suspension of 3-hydroxy-1-(1-piperidinylmethyl)benzocyclobutene (1.0 g), and tetrabutylammonium chloride (0.13 g) in 1,3-dibromopropane (4.6 ml) and the resulting mixture stirred at RT under nitrogen for two days. The reaction mixture is partitioned between ice-water and ether and the aqueous layer separated and extracted with ether. The combined organic extract is washed with water, ice cold 5% aqueous HCl thereby forming a precipitate which is filtered and washed with ether. The acidic layer is alkalized forming an oily precipitate which is taken up in ether. The combined ether fractions are washed with water, dried over Na$_2$SO$_4$, filtered and concentrated in vacuo yielding the desired product as an oil which is used in the next step without further purification.

Step 12.
5-(3-Azidopropoxy)-1-(1-piperidinylmethyl)benzocyclobutene

Sodium azide (0.8 g) is added to a stirred solution of 5-(3-bromopropoxy)-1-(1-piperidinylmethyl)benzocyclobutene (0.8 g) (from Step 11 above) in ethanol/water (16 ml/1.6 ml) and the mixture heated to reflux for 24 hours. The reaction mixture is cooled and partitioned between water and methylene chloride. The organic layer is separated, washed with water, dried over Na$_2$SO$_4$, filtered and concentrated in vacuo yielding the desired azido compound as an oil.

Step 13.
5-(3-Aminopropoxy)-1-(1-piperidinylmethyl)benzocyclobutene

A solution of the azido cyclobutene (0.7 g) (of Step 12 above) in ether (2.5 ml) is added over a period of about 30 min to a suspension of 0.15 g LAH in anhydrous ether (30 ml) stirred under nitrogen. The mixture is refluxed for about 1.5 hours and cooled. Water (0.15 ml), aqueous NaOH (15% solution, 0.15 ml) and water (0.45 ml) are added to the reaction mixture and stirring continued for about one hour. The mixture is filtered, the solid washed with ether and the filtrate dried over Na$_2$SO$_4$. The dried ether extract is filtered, concentrated in vacuo, and the residue is dissolved in methylene chloride, dried, filtered and concentrated yielding the desired product as an oil.

EXAMPLE 2

The Alternate Preparation of 5-(3-Aminopropoxy)-1-(1-Piperidinylmethyl)Benzocyclobutene

Step 1.
5-Methoxy-1-(1-piperidinylcarbonyl)benzocyclobutene

Thionyl chloride (168.6 ml) is added dropwise to a stirred solution of 5-methoxybenzocyclobutene-1-carboxylic acid (162 g) in methylene chloride (1.3 l) cooled to 0° C. under nitrogen. The solution is refluxed under nitrogen for 2.5 hours, evaporated and the residual oil dissolved in methylene chloride (1.3 l), and the solution added slowly to an ice cold solution of piperidine (500 ml) in methylene chloride (1.3 l). The reaction mixture is stirred overnight, washed with saturated NaHCO$_3$ and 5% aqueous NaOH, the aqueous fractions combined and acidified resulting in an oil, which is taken up in methylene chloride. The methylene chloride solution is washed, dried, filtered and evaporated in vacuo. The residue is chromatographed (silica gel 600 g: ethyl acetate/hexane) yielding the desired product as an oil.

Step 2.
5-Hydroxy-1-(1-piperidinylcarbonyl)benzocyclobutene

Trimethylsilyliodide (74.3 ml) is added dropwise to a stirred solution of the 5-methoxy compound obtained in the step above (64 g) and acetonitrile (500 ml) under nitrogen. The reaction mixture is refluxed for five hours, diluted with methylene chloride (1.5 l), washed with 10% aqueous NaHSO$_3$, dried, filtered and evaporated in vacuo to a yellow solid. The solid is recrystallized from acetonitrile, identified by NMR to be the desired product, and used as is in the next step.

Step 3.
5-(3-Bromopropoxy)-1-(1-piperidinylcarbonyl)benzocyclobutene

Potassium hydroxide (1.23 g) is added slowly to a stirred solution of 5-hydroxy-1-(1-piperidinylcarbonyl)benzocyclobutene (3.4 g) and tetrabutylammonium chloride (0.5 g) in 1,3-dibromopropane (14.9 ml) and methylene chloride (30 ml) cooled in an ice bath. The reaction mixture is stirred at RT under nitrogen overnight, diluted with methylene chloride, washed with water, dried, filtered and evaporated in vacuo affording a liquid. The liquid is chromatographed (silica gel:hexane/ethyl acetate) yielding the desired bromopropoxy compound as an oil, which is used in the next step without further purification.

Step 4.
5-(3-Azidopropoxy)-1-(1-piperidinylcarbonyl)benzocyclobutene

Sodium azide (2.4 g) is added to a stirred solution of 5-(3-bromopropoxy)-1-(1-piperidinylcarbonyl)benzocyclobutene (12.8 g) in ethanol/water (13 ml/130 ml). The reaction mixture is refluxed overnight, poured into water, washed with methylene chloride and the organic extract washed, dried, filtered and evaporated in vacuo affording the desired azide product as an oil, which is used in the next step without further purification.

Step 5.
5-(3-Aminopropoxy)-1-(1-piperidinylmethyl)benzocyclobutene

A solution of the azidocyclobutene of the previous step (10.0 g) in anhydrous THF (64 ml) is added dropwise to a stirred suspension of LAH (3.04 g) in anhydrous ether (400 ml) under nitrogen. The reaction mixture is refluxed overnight, quenched with $H_2O$ (3 ml), 15% sodium hydroxide (3 ml) and water (9 ml), filtered, dried, filtered, concentrated in vacuo and the residue chromatographed (silica gel:methanol) yielding the desired product as an oil.

EXAMPLE 3
The Preparation of 3-(3-Aminopropoxy)-1-(1-Piperidinylmethylbenzocyclobutene

Step 1. 4-(3-Chloropropoxy)-1-indanone

1-Bromo-3-chloropropane (17.3 g) is added to a stirred mixture of 4-hydroxyindanone (14.8 g), potassium carbonate (15.3 g) in DMF/water (150 ml/50 ml) and the reaction mixture stirred at RT for about 4 days. The reaction mixture is partitioned between water and methylene chloride and the organic layer is separated, dried, filtered and evaporated, affording a residue which is chromatographed on a silica gel column to yield the desired product as a white solid.

Step 2. 4-(3-Chloropropoxy)-2-oxime-1-indanone 12.5 g of n-butyl nitrite is added to a stirred solution of 4-(3-chloropropoxy)-1-indanone (17.6 g) and hydrochloric acid (12N, 39.2 ml) in methoxyethanol (315 ml) and the mixture stirred at RT for 2 hours. The reaction mixture is poured into water, cooled to 0° C. in an ice bath resulting in the formation of a precipitate which is filtered, washed with water and dried yielding the desired oxime product as a yellow crystalline solid.

Step 3. 3-(Chloropropoxy)-2-diazo-1-indanone

Ammonium hydroxide (8.74 ml, 15N) is added to a stirred mixture of 4-(3-chloropropoxy)-2-oxime-1-indanone (16.6 g) and sodium hydroxide (2.6 g) in water (500 ml) at 2° C. Sodium hypochlorite (218 ml, 5.25% aqueous solution) is added slowly to the reaction mixture maintained at about 2° C. and allowed to stand at RT for about 4 hours. The reaction mixture is filtered and the solid washed with water. The solid is dissolved in methylene chloride, filtered, dried over $Na_2SO_4$, and evaporated in vacuo resulting in the desired product as a solid.

Step 4.
3-(3-Chloropropoxy)benzocyclobutene-1-carboxylic acid

A solution of 3-(chloropropoxy)-2-diazo-1-indanone (11.4 g) and sodium bicarbonate (9.4 g) in a solvent mixture of THF (800 ml) and water (140 ml) is photolyzed for 63 hours. The THF is evaporated in vacuo and the aqueous remainder partitioned between water and methylene chloride. The aqueous layer is acidified with conc. HCl and extracted with methylene chloride. The methylene chloride extract is washed with saturated NaCl, dried over $Na_2SO_4$, filtered and concentrated in vacuo yielding the desired carboxylic acid as an oil.

Step 5.
3-(3-Chloropropoxy)-1-hydroxymethylbenzocyclobutene

A solution of 3-(3-chloropropoxy)benzocyclobutene-1-carboxylic acid (2.6 g) in THF (25 ml) is added to a stirred suspension of LAH (0.9 g) in 40 ml of ether under nitrogen. The reaction mixture is stirred at RT for 4 hours, and quenched with water (0.9 ml), 15% NaOH solution (0.9 ml) and water (2.6 ml). The reaction mixture is filtered and the ether/THF evaporated in vacuo. The residue is extracted with methylene chloride, the organic extract dried over $Na_2SO_4$, filtered and the solvent evaporated in vacuo yielding the desired product as an oil.

Step 6.
3-(3-Chloropropoxy)-1-hydroxymethylbenzocyclobutene mesylate

Methane sulfonylchloride (1.13 g) is added dropwise to a stirred solution of 3-(3-chloropropoxy)-1-hydroxymethylbenzocyclobutene (1.83 g) and triethylamine (1.58 ml) in methylene chloride (32 ml) at 5° C. under nitrogen. The reaction mixture is stirred at RT for about 2 hours, washed with water, saturated NaCl, dried over $Na_2SO_4$, filtered and evaporated in vacuo yielding the desired product as an oil.

Step 7.
3-(3-Chloropropoxy)-1-(1-piperidinylmethyl)benzocyclobutene

Piperidine (3.19 ml) is added to a solution of 3-(3-chloropropoxy)-1-hydroxymethylbenzocyclobutene mesylate (2.45 g) in toluene (32 ml) and the reaction mixture refluxed under nitrogen for about 12 hours. The reaction mixture is diluted with ethyl acetate and extracted with saturated $NaHCO_3$ followed by saturated NaCl. The organic extract is dried, filtered and concentrated yielding the crude product used in the next step.

Step 8.
3-(3-Azidopropoxy)-1-(1-piperidinylmethyl)benzocyclobutene

Sodium iodide (3 g) is added to a stirred solution of 3-(3-chloropropoxy)-1-(1-piperidinylmethyl)benzocyclobutene (0.87 g) in 12 ml of DMF. The reaction mixture is stirred under nitrogen for 12 hours, sodium azide (1.17 g) is added to this solution followed by water (1.2 ml). The resulting suspension is heated at 75° C. for 5 hours. The reaction mixture is partitioned between water and methylene chloride and the organic layer is separated, washed, dried, filtered and evaporated in vacuo yielding the azide product as an oil.

Step 9.
3-(3-Aminopropoxy)-1-(1-piperidinylmethyl)benzocyclobutene

A solution of the azido benzocyclobutenylmethyl compound (0.8 g) (step 8 above) in THF (5.2 ml) is added over a period of 30 min to a suspension of LAH (0.125 g) in anhydrous ether (16.5 ml) stirred under nitrogen. The mixture is refluxed for about 2 hours and cooled. Water (0.125 ml), aqueous NaOH (15% solution, 0.125 ml) and water (3.75 ml) are added to the cooled mixture which is filtered. The solid is washed with ether and the filtrate dried over $Na_2SO_4$. The dried filtrate is filtered, evaporated in vacuo and chromatographed (silica gel) eluting with 1:1 ethyl acetate/MeOH. The pure fractions are combined and evaporated in vacuo yielding an oil. NMR analysis identifies the oil as the desired product.

EXAMPLE 4

The Alternate Preparation of 3-(3-Aminopropoxy)-1-(1-Piperidinylmethyl)Benzyocyclobutene

Step 1.
3-(3-Chloropropoxy)-1-(1-piperidinylcarbonyl)benzocyclobutene

Thionyl chloride (1.98 g) is added dropwise to a stirred solution of 3-(3-chloropropoxy)benzocyclobutene-1-carboxylic acid (1.6 g) in methylene chloride maintained at about 0° C. The reaction mixture is refluxed for two hours, evaporated, the residue dissolved in methylene chloride, and the methylene chloride solution added dropwise to a stirred solution of piperidine (6.65 g) in methylene chloride (13.3 ml) maintained at about 0° C. The reaction mixture is allowed to stand at RT overnight, diluted with methylene chloride and extracted with aqueous hydrochloric acid (1N). The aqueous fraction is neutralized and the resulting oil is extracted with methylene chloride. The organic extract is evaporated and the residue used as is in the next step.

Step 2.
3-(3-Azidopropoxy)-1-(1-piperidinylcarbonyl)benzocyclobutene

A solution of 3-(3-chloropropoxy)-1-(1-piperidinylcarbonyl)benzocyclobutene (1.4 g), potassium iodide (4.5 g) and dimethylformamide (18.2 ml) is stirred at RT for 24 hours. Sodium azide (1.78 g) and H$_2$O (1.82 ml) are added to the stirred mixture, which is heated for five hours at 75° C. The reaction mixture is poured into a solution of 10% NaHSO$_3$/NaHCO$_3$ and extracted with methylene chloride. The organic layer is separated, washed, dried, filtered and evaporated in vacuo yielding the azide product as an oil.

Step 3.
3-(3-Aminopropoxy)-1-(1-piperidinylmethyl)benzocyclobutene

A solution of the azidobenzocyclobutenylamide compound of Step 2. above (3.2 g) in THF (20.4 ml) is added dropwise to a suspension of LAH (0.93 g) in anhydrous ether (122 ml) stirred under nitrogen maintained at ice bath temperatures. The reaction mixture is refluxed for 15 hours, cooled and quenched with water (0.93 ml), aqueous sodium hydroxide (15% solution, 0.93 ml) and water (2.79 ml) and filtered. The solid is washed with ether and the combined filtrate dried, filtered, evaporated in vacuo and chromatographed (silica gel: ethyl acetate/methanol). The pure fractions are combined and evaporated in vacuo yielding an oil, which is identified at the desired product by NMR.

EXAMPLE 5

The Preparation of 3-Amino-5-[3-[3'-[1-[1-Piperidinylmethyl]]Benzocyclobutenyloxy]Propylamino]]-1-Methyl-1H-1,2,4-Triazole 3-[3-Aminopropoxy]-1-(1-piperidinylmethyl)benzocyclobutene (1.5 g) and N-cyano-1-methyl-2-phenylmethylenehydrazinecarboximidethioic acid methyl ester are dissolved in CH$_2$Cl$_2$ and evaporated in vacuo. The neat mixture is heated to 70° C. for four hours and the resultant glass is dissolved in 5% aqueous HCl (30 ml)/acetone (20 ml) and washed with ether. The aqueous solution is made alkaline resulting in a yellow oil which is taken up in ethyl acetate, washed with saturated salt, dried over Na$_2$SO$_4$, filtered and evaporated in vacuo to a yellow oil which is chromatographed (silica gel, 1/1:MeOH/EtOAc). The purified fractions are combined and evaporated to a glass which is triturated with ether yielding the desired product as a solid, M.P.=114°–116° C.

EXAMPLE 6

The Preparation of 5-(3-Aminopropoxy)-2-Methyl-1-(1-Piperidinylmethyl)Benzocyclobutene

Step 1. 3-(4-Methoxyphenyl)-2-butenenitrile

Diethylcyanomethylphosphonate (85 g) is added dropwise to a stirred suspension of sodium hydride (19.2 g) in 1,2-dimethoxyethane (400 ml) under nitrogen. The solution is cooled in an ice bath and a solution of paramethoxyacetophenone (48 g) in 1,2-dimethoxyethane (80 ml) is added dropwise. The reaction mixture is stirred at RT for three hours and diluted with diethyl ether, washed, dried, filtered and evaporated in vacuo affording the desired product as a solid.

Step 2. 3-(4-Methoxyphenyl)-2-butenenitrile

A solution of the butenenitrile of the previous step (53 g) and 5% palladium on carbon (5.3 g) in absolute ethanol (530 ml) is placed under 54 lbs. of hydrogen pressure for nine hours, filtered through Celite ® and allowed to stand overnight. The solution is evaporated in vacuo affording an oil, which is used as is in the next step.

Step 3. 1-Bromo-5-[3-butenenitrile]-2-methoxybenzene

Bromine (14.9 ml) is added dropwise over a period of one hour to a stirred solution of the butenenitrile obtained in the previous step (51 g) and sodium acetate (47.7 g) in glacial acetic acid (300 ml). The reaction mixture is stirred for 30 minutes and poured into water (600 ml), extracted with ether and the organic extract washed with sat'd NaHCO$_3$ and 10% aqueous NaOH. The organic extract is dried, filtered and evaporated in vacuo to an oil which is distilled (170° C., ≦1 mm) affording the desired product as a yellow oil.

Step 4.
1-Cyano-5-methoxy-2-methyl-benzocyclobutene

The bromo compound obtained in the previous step (61.8 g) is added dropwise over a period of 30 minutes to a refluxing suspension of sodium amide (39.8 g) in liquid ammonia (500 ml) under nitrogen, and the reaction mixture refluxed (−33° C.) for three hours. The reaction mixture is quenched with ammonium chloride (52.4 g) and allowed to evaporate overnight. The residue is taken up in water (1 l) and washed with chloroform. The chloroform extract is washed with aqueous hydrochloric acid, dried, filtered, stirred with silica gel, filtered and evaporated in vacuo affording a brown oil, which is chromatographed (silica gel: ethyl acetate/hexane) to give a brown oil, which is used as is in the next step.

Step 5.
5-Methoxy-2-methyl-benzocyclobutene-1-carboxylic acid

The cyanobenzocyclobutene compound obtained in the previous step (45.6 g) is dissolved in ethanolic sat'd potassium hydroxide (300 ml) and stirred at RT under nitrogen overnight. The reaction mixture is diluted with water, refluxed for 30 hours, poured into water, extracted with ether and the aqueous layer acidified and extracted with ether. The ethereal extract is washed, dried, filtered and evaporated in vacuo affording the desired product as an oil, which is identified by NMR.

Step 6.
2-Methyl-5-methoxy-1-(piperidinylcarbonyl)benzocyclobutene

Oxalyl chloride (40.9 ml) is added dropwise to a stirred solution of the benzocyclobutene carboxylic acid obtained in the previous step (90.2 g) dissolved in a mixture of DMF (3 ml) and methylene chloride (450 ml). The reaction mixture is stirred at RT overnight and added dropwise to an ice cold solution of piperidine (185 ml) in methylene chloride (450 ml) over a 90-minute period. The reaction mixture is allowed to stir at RT for five hours, washed with aqueous 5% hydrochloric acid, dried, filtered and evaporated affording the desired product as an oil, which is used in the next step without further purification.

Step 7.
5-Methoxy-2-methyl-1-(1-piperidinylmethyl)benzocyclobutene

A solution of the piperidinylcarbonyl compound obtained in the previous step (6.4 g) in THF (100 ml) is added slowly to a stirred suspension of LAH (1.07 g) in THF (15 ml) under nitrogen. The reaction mixture is heated to reflux for two hours, and an additional amount of LAH (0.46 g) is added to the suspension and stirring continued for an additional hour. The reaction mixture is quenched, filtered, dried, filtered and evaporated in vacuo affording the desired product as a yellow oil.

Step 8.
5-Hydroxy-2-methyl-1-(1-piperidinylmethyl)benzocyclobutene

Trimethylsilyliodide (11.8 ml) is added to a stirred solution of the piperidinylmethylbenzocyclobutene compound of the previous step (9.5 g) dissolved in acetonitrile (90 ml) under nitrogen. During the addition, the reaction mixture is heated, thereby removing generated methyliodide, over a period of two hours. The reaction mixture is allowed to cool, diluted with methylene chloride extracted with 10% aqueous NaHSO$_3$ and 5% aqueous HCl. The aqueous extract is washed with methylene chloride, basified to pH 8–10, and the basic fraction extracted with methylene chloride. The organic extract is washed, dried over magnesium sulphate, filtered and evaporated in vacuo yielding an oil which is used as is in the next step.

Step 9.
5-(3-Bromopropoxy)-2-methyl-1-(1-piperidinylmethyl)benzocyclobutene

Aqueous potassium hydroxide (45%) is added to a stirred solution of the hydrochloride salt of the piperidinylmethylbenzocyclobutene obtained in the preceding step (6.5 g) in methylene chloride (30 ml) under nitrogen. The solution is stirred at RT for 30 minutes, and tetrabutylammonium chloride (0.9 g) and 1,3-dibromopropane (26 ml) are added to the stirred reaction mixture. The reaction mixture is stirred for an additional 2.5 hours, diluted with methylene chloride, washed with water, and extracted with 5% aqueous HCl. The acidic extract is washed with ether and basified affording a cloudy solution, which is extracted with methylene chloride. The organic extract is washed with sat'd NaCl solution, dried, filtered and evaporated in vacuo affording the desired product as an oil.

Step 10.
5-(3-Azidopropoxy)-2-methyl-1-(1-piperidinylmethyl)benzocyclobutene Sodium azide (1.49 g) is added to a stirred solution of 5-(3-bromopropoxy)-2-methyl-1-(1-piperidinylmethyl)benzocyclobutene (7.3 g) dissolved in a mixture of ethanol/water (7.3 ml/73 ml). The reaction mixture is refluxed overnight, poured into water and extracted with ether. The organic extract is washed with sat'd aqueous NaCl, dried, filtered and evaporated in vacuo affording the desired product as an oil.

Step 11.
5-(3-Aminopropoxy)-2-methyl-1-(1-piperidinylmethyl)benzocyclobutene A solution of the azidocyclobutene obtained in the previous step (5.3 g) in anhydrous THF (15 ml) is added dropwise to a suspension of LAH (0.88 g) in anhydrous diethylether (200 ml) under nitrogen. The reaction mixture is refluxed for one hour, quenched, filtered, dried, filtered and evaporated in vacuo. The residue is chromatographed (silica gel: 5% triethylamine in methanol) affording the desired product as identified by NMR as an oil.

EXAMPLE 7

The Preparation of
5-(3-Aminopropoxy)-1,2-Dimethyl-1-(1-Piperidinylmethyl)Benzocyclobutene

Step 1.
5-Methoxy-1,2-dimethyl-1-(1-piperidinylcarbonyl)benzocyclobutene

A solution of n-butyllithium in hexane (2.5M, 77.3 ml) is added dropwise to a stirred solution of diisopropyl amine (21.29 g) in THF (400 ml) under nitrogen at −78° C. A 1M solution of 5-methoxy-2-methyl-1-(1-piperidinylcarboxyl)benzocyclobutene (45.5 g) in THF is added to the cooled solution. The reaction mixture is stirred for 15 minutes at −78° C. and neat methyl iodine (54.88 g) is added dropwise. The reaction mixture is allowed to warm RT, extracted with water, washed with brine, dried, filtered, and the filtrate evaporated in vacuo yielding an oil which is used in the next step without further purification.

Step 2.
1,2-Dimethyl-5-methoxy-1-(1-piperidinylmethyl)benzocyclobutene

A solution of the 1,2-dimethyl compound obtained in Step 1. above (43.8 g) in anhydrous THF (640 ml) is added dropwise to a suspension of LAH (7.6 g) in anhydrous THF (200 ml). The reaction mixture is heated to reflux for 45 minutes, cooled and quenched with water, aqueous NaOH (15%), and water. The reaction mixture is filtered, evaporated in vacuo and chromatographed (silica gel: ethyl acetate/hexane) and the major fractions combined, and evaporated yielding the desired product as an oil which is identified by NMR. The oil is dissolved in methanolic hydrochloric acid, the methanolic solution evaporated and the residue recrystallized (acetonitrile/ether), M.P.=179°–181° C.

Step 3.
1,2-Dimethyl-5-hydroxy-1-(1-piperidinylmethyl)benzocyclobutene

Trimethylsilyliodide (39.3 g) is added dropwise to a stirred refluxing solution of the 5-methoxy compound obtained in the previous step (25.4 g) in acetonitrile (200 ml) for 2.5 hours while removing generated methyl iodide. The reaction is quenched with methanol, diluted with methylene chloride and extracted with a mixture of 10% $NaHSO_3$/sat'd $NaHCO_3$. The organic layer is dried, filtered and evaporated yielding the desired product as an oil which is used in the next step without further purification.

Step 4.
5-(3-Bromopropoxy)-1,2-dimethyl-1-(1-piperidinylmethyl)benzocyclobutene

Dibromopropane (143.6 g) is added dropwise to a stirred solution of the hydroxy compound obtained in the previous step (17.4 g), potassium hydroxide (5.16 g, 85%) and tetrabutylammonium chloride (2.48 g, 85%) in methylene chloride (142 ml) for 24 hours at RT under nitrogen. The reaction mixture is diluted with methylene chloride, extracted with water, dried, filtered and evaporated. The residue is chromatographed (silica gel: ethyl acetate/hexane) and the major fractions combined, and evaporated yielding the desired product as an oil which is used in the next step without further purification.

Step 5.
5-(3-Azidopropoxy)-1,2-dimethyl-1-(1-piperdinylmethyl)benzocyclobutene

An aqueous solution of sodium azide (2.8 g) in $H_2O$ (14 ml) is added to a stirred solution of the bromo compound obtained in the previous step (14.3 g) in ethanol (140 ml). The reaction mixture is refluxed overnight under nitrogen, poured into water and extracted with methylene chloride. The organic extract is dried over sodium sulfate, filtered and evaporated to an oil which is used without further purification in the next step.

Step 6.
5-(3-Aminopropoxy)-1,2-dimethyl-1-(1-piperidinylmethyl)benzocyclobutene

A solution of the azide obtained in the previous step (11.9 g) in THF (145 ml) is added to a one molar suspension of LAH (1.74 g) in THF (44 ml). The reaction mixture is refluxed under nitrogen for one hour, cooled, quenched with water, 15% aqueous sodium hydroxide and water and filtered. The filtrate is evaporated and the residue chromatographed (silica gel: methanol). The slower moving fractions are combined and evaporated to an oil which is identified as the desired product. NMR ($CDCl_3$, TMS) δ 1.25(d,3H) 1.4(s,3H), 1.32–1.68(m,6H), 1.95(m,2H), 2.35–2.65(m,4H), 2.48(s,2H), 2.9(t,2H), 3.1(q,1H), 4.0(t,2H), 6.75(dd,2H), 6.98(d,1H).

EXAMPLE 8

The Preparation of
1-Allyl-5-(3-Aminopropoxy)-1-(1-Piperidinylmethyl)-Benzocyclobutene Step 1.
5-(3-Chloropropoxy)-1-(1-piperidinylcarbonyl)benzocyclobutene Tetrabutylammonium chloride (4.48 g) and 1-bromo-3-chloropropane (127.8 ml) are added to a stirred solution of 5-hydroxy-1-(1-piperidinylcarbonyl)benzocyclobutene (31.8 g) in methylene chloride (250 ml) and potassium hydroxide (18.85 g, 45% in $H_2O$) which has been stirred vigorously under nitrogen for one hour. The reaction mixture is stirred at RT overnight, diluted with methylene chloride, extracted with $H_2O$, sat'd aqueous NaCl and the organic layer dried over sodium sulfate. The solution is filtered, evaporated in vacuo and chromatographed (silica gel: ethyl acetate/hexane) yielding the desired product as an oil which is identified by NMR.

Step 2.
1-Allyl-5-(3-chloropropoxy)-1-(1-piperidinylcarbonyl)-benzocyclobutene

A solution of n-butyl lithium in hexane, (2.5M, 28.6 ml) is added dropwise to a stirred solution of diisopropylamine (11.4 ml) in THF (195 ml) cooled to −78° C. under nitrogen and stirred for ten minutes. A solution of the chloropropoxy compound obtained in the preceeding step (20 g) in THF (160 ml) is added dropwise to the stirred solution over a period of 20 minutes and stirring contined for 15 minutes. Allyl bromide (12.3 ml) is added dropwise to the solution which is stirred at RT for two hours, diluted with diethyl ether, washed with water, sat'd aqueous NaCl and the organic layer dried over sodium sulfate. The dried extract is filtered, evaporated in vacuo, and chromographed (silica gel: ethyl acetate/hexane) affording the desired product as an oil which is identified by NMR.

Step 3.
1-Allyl-5-(3-azidopropoxy)-1-(1-piperidinylcarbonyl)-benzocyclobutene

A solution of the 1-allyl, 5-chloropropoxy compound obtained in the preceeding step (0.9 g), sodium iodide (0.8 g) and sodiumazide (0.7 g) in DMSO (9 ml) is stirred under nitrogen at 90° C. for 4.5 hours. The reaction mixture is poured into water, washed with ether and the ethereal extract back extracted with water. The organic extract is dried over sodium sulfate, filtered and evaporated in vacuo affording the desired product as an oil which is used as is in the next step without further purification.

Step 4.
1-Allyl-5-(3-aminopropoxy)-1-(1-piperidinylmethyl)-benzocyclobutene

A solution of 1-allyl-5-(3-azidopropoxy)1-(1-piperidinylcarbonyl)benzocyclobutene (19.5 g) in THF (200 ml) is added dropwise to a stirred suspension of LAH (5.26 g) in THF (82 ml) under nitrogen. The reaction mixture is refluxed for one hour, quenched with water, 15% aqueous NaOH and water, filtered and evaporated in vacuo affording an oil which is chromatographed (silica gel: 5% triethylamine/methanol) affording the desired product as an oil.

The diamine compounds described above (where Z=NH₂) can be used without further purification to prepare additional benzocyclobutene compounds of Formula I. Examples of compounds where Z is NHR₇ (other than hydrogen) are described in Table B below.

TABLE B

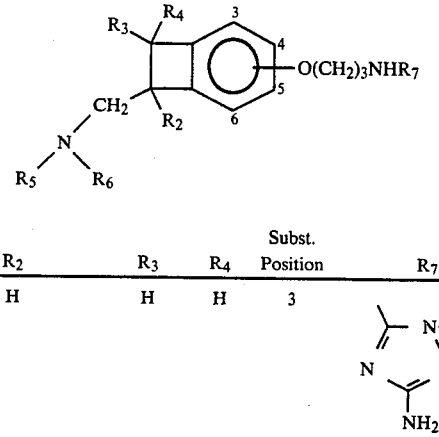

| R₅ R₆ | R₂ | R₃ | R₄ | Subst. Position | R₇ | M.P. |
|---|---|---|---|---|---|---|
| —(CH₂)₅— | H | H | H | 3 | 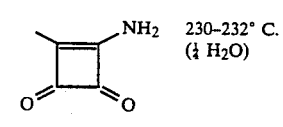 | 114–116° C. |
| —(CH₂)₅— | H | H | H | 5 | 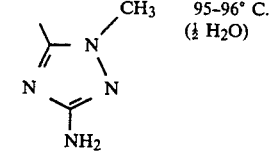 | 230–232° C. (¼ H₂O) |
| —(CH₂)₅— | H | H | H | 5 | 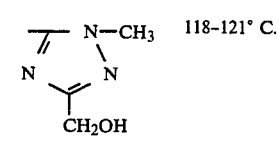 | 95–96° C. (½ H₂O) |
| —(CH₂)₅— | H | H | H | 5 | 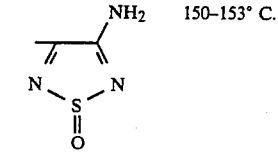 | 118–121° C. |
| —(CH₂)₄— | H | H | H | 5 | 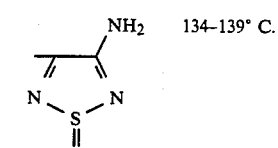 | 150–153° C. |
| CH₃ CH₃ | H | H | H | 5 | 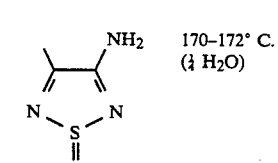 | 134–139° C. |
| —(CH₂)₅— | H | H | H | 3 | 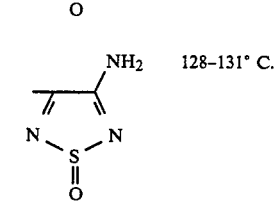 | 170–172° C. (¼ H₂O) |
| —(CH₂)₅— | benzyl | H | H | 5 | | 128–131° C. |

TABLE B-continued

Structure:

R3, R4 on cyclobutane fused to benzene ring; benzene positions 3,4,5,6; substituent O(CH2)3NHR7; CH2-N(R5)(R6) group with R2.

| R5 | R6 | R2 | R3 | R4 | Subst. Position | R7 | M.P. |
|---|---|---|---|---|---|---|---|
| —(CH2)5— | | benzyl | H | H | 5 | 1-methyl-3-amino-1,2,4-triazol-5-yl | 144–145° C. |
| —(CH2)5— | | CH3 | CH3 | H | 5 | 4-amino-3-methyl-1,2,5-thiadiazole 1-oxide | 115–117° C. |
| —(CH2)5— | | CH3 | CH3 | H | 5 | 1-methyl-3-amino-1,2,4-triazol-5-yl | 68–70° C. |
| CH3 | CH3 | H | H | H | 5 | 1-methyl-3-amino-1,2,4-triazol-5-yl | "glass" |
| —(CH2)4— | | H | H | H | 5 | 1-methyl-3-amino-1,2,4-triazol-5-yl | "glass" |
| —(CH2)5— | | —CH2—N(piperidine) | H | H | 5 | 4-amino-3-methyl-1,2,5-thiadiazole 1-oxide | |
| —(CH2)5— | | —CH2—N(piperidine) | H | H | 5 | 1-methyl-3-amino-1,2,4-triazol-5-yl | |
| —(CH2)5— | | —CH2—OH | H | H | 5 | 4-amino-3-methyl-1,2,5-thiadiazole 1-oxide | |

TABLE B-continued

Structure: bicyclic benzocyclobutane with R3, R4 at positions 3; substituent —O(CH2)3NHR7 at position 4 or 5; CH2—N(R5)(R6) group and R2 at the cyclobutane ring.

| R5 | R6 | R2 | R3 | R4 | Subst. Position | R7 | M.P. |
|---|---|---|---|---|---|---|---|
| —(CH2)5— | | —CH2—OH | H | H | 5 | 4-amino-1-methyl-5-(1,2,4-triazin-3-yl-guanidine) group (methyl-N—CH3 triazine with NH2) | |
| —(CH2)5— | | —(CH2)2—OH | H | H | 5 | 4-amino-3-methyl-1,2,5-thiadiazole 1-oxide | |
| —(CH2)5— | | —(CH2)2—OH | H | H | 5 | methyl-triazine with N—CH3 and NH2 | |
| —(CH2)5— | | H | C6H5 | H | 5 | 4-amino-3-methyl-1,2,5-thiadiazole 1-oxide | |
| —(CH2)5— | | H | C6H5 | H | 5 | methyl-triazine with N—CH3 and NH2 | |
| —(CH2)5— | | H | CH3 | CH3 | 5 | 4-amino-3-methyl-1,2,5-thiadiazole 1-oxide | |
| —(CH2)5— | | H | CH3 | CH3 | 5 | methyl-triazine with N—CH3 and NH2 | |
| —(CH2)5— | | m-C3H7 | H | H | 5 | 4-amino-3-methyl-1,2,5-thiadiazole 1-oxide | |

TABLE B-continued
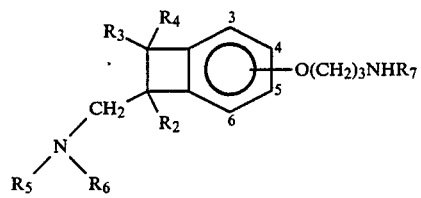
| R5 | R6 | R2 | R3 | R4 | Subst. Position | R7 | M.P. |
|---|---|---|---|---|---|---|---|
| —(CH2)5— | | m-C3H7 | H | H | 5 | 3-amino-1,5-dimethyl-1,2,4-triazole | |
| —(CH2)5— | | C2H5 | H | H | 5 | 4-amino-3-methyl-1,2,5-thiadiazole 1-oxide | |
| —(CH2)5— | | C2H5 | H | H | 5 | 3-amino-1,5-dimethyl-1,2,4-triazole | |
| —(CH2)5— | | H | C2H5 | H | 5 | 4-amino-3-methyl-1,2,5-thiadiazole 1-oxide | |
| —(CH2)5— | | H | C2H5 | H | 5 | 3-amino-1,5-dimethyl-1,2,4-triazole | |
| —(CH2)5— | | H | m-C3H7 | H | 5 | 4-amino-3-methyl-1,2,5-thiadiazole 1-oxide | |
| —(CH2)5 | | H | m-C3H7 | H | 5 | 3-amino-1,5-dimethyl-1,2,4-triazole | |
| —(CH2)5— | | —(CH2)2—OCH3 | m-C3H7 | H | 5 | 4-amino-3-methyl-1,2,5-thiadiazole 1-oxide | |

TABLE B-continued

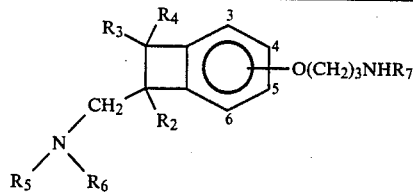

| $R_5$ | $R_6$ | $R_2$ | $R_3$ | $R_4$ | Subst. Position | $R_7$ | M.P. |
|---|---|---|---|---|---|---|---|
| $-(CH_2)_5-$ | | $-(CH_2)_2-OCH_3$ | m-$C_3H_7$ | H | 5 | 2-amino-1-methyl-imidazolyl | |
| $-(CH_2)_5-$ | | $-CH_2-CO_2Et$ | m-$C_3H_7$ | H | 5 | 4-amino-1,2,5-thiadiazole 1-oxide | |
| $-(CH_2)_5-$ | | $-CH_2-CO_2Et$ | m-$C_3H_7$ | H | 5 | 2-amino-1-methyl-imidazolyl | |

Various tests in animals have been carried out to show the ability of the compounds of this invention to exhibit pharmacological responses that can be correlated with activity in humans. These tests involve such factors as the effect of the compounds of Formula I on gastric secretion and their $H_2$ antagonist and cytoprotective activity. It has been found that the compounds of this invention when tested in the above variety of situations show a marked activity.

One such test is the gastric secretion test. This test is carried out as follows: Shay rats are fasted for 4–8 hours, and water is given ad lib. The rats are selected at random and separated into groups of 10. The animals are treated intraduodenally (I.D.) with the test compounds or the vehicle immediately subsequent to the ligation of the stomach at the pyloric sphincter. The animals are sacrificed with chloroform at 4 hours post-drug administration, the stomach removed and its contents assayed for volume, pH and total acids.

A second gastric secretion test is carried out on the dog. This is outlined in the *Handbook of Physiology*, Section 6: Alimentary Canal, Volume II: Secretion. American Physiology Society, Washington, D.C., 1967.

It has been found that the compounds of this invention, when subjected to the above gastric secretion tests, display marked ability to decrease gastric volume and gastric acidity. These tests are known to correlate well with gastric activity in humans and are standard tests used to determine anti-secretory properties.

The compounds of Formula I have been found to be histamine $H_2$-receptor antagonists by the results obtained in the following $H_2$-antagonist tests.

A. Isolated Guinea Pig Atria

The $H_2$-receptor antagonist activity of the compounds of Formula I is measured by observing the beat rate response versus compound concentration in isolated guinea pig atria. A discussion of criteria to evaluate these dose-response curves may be found in, E. J. Ariens, G. A. J. vanOs, A. M. Simonis, and T. M. van Rossum, "A Molecular Approach to General Pharmacology", Sections 11A, 11B, and 111, *Molecular Pharmacology: The Mode of Action of Biologically Active Compound*. Vol. 1, Academic Press (1964).

1. Tissue Bath

A fifty ml jacketed tissue bath is maintained at 30° C. The bath consists of a Krebs-Henseleit buffer aerated with 95% $O_2$–5% $CO_2$, (pH 7.4). The buffer is prepared by mixing: 4 ml of an aqueous (distilled deionized) solution of $CaCl_2.2H_2O$ (0.37 g/ml); 4 ml of an aqueous (distilled deionized) solution of $MgSO_4.7H_2O$ (0.29 g/ml); 7.2 g of glucose; and, 2 liters of aqueous (distilled deionized) solution containing NaCl (28 g), $NaHCO_2$ (8.4 g), KCl (1.4 g) and $KH_2PO_4$ (0.6 g).

2. Preparation of Atria

Male albino guinea pigs (400–700 g, preferably 500–600 g) are killed by a flow to the back of the head and exsanguinated by cutting jugular veins and carotid arteries. The thoracic skin is opened from this neck cut and the rib cage exposed. Both sides of the rib cage and the diaphragm are cut and laid back, exposing the heart. The heart is removed by cutting through the vessels above and behind it while it is slightly elevated with forceps holding the ventricle tip. The heart is immediately placed in warm, aerated buffer and further dissected in a large petri dish of the same buffer. Since the pericardium is removed, it is possible to slip iris scissors between the atria and ventricles while holding the aorta and vessels with tweezers and cut off the atria. The atria are then dissected from any remaining tissue and vessels and suspended in the bath using small, curved taperpoint needles formed into hooks and tied to an S-shaped hook and the L-shaped lower support with 00 silk.

A Beckman Type 9308 Strain Gauge Coupler connects a Beckman cardiotachometer to a Grass FT03C strain gauge supported in a rack and pinion clamp. The upper hook of the strain gauge is placed in the edge of the left atrium and the lower hook in the tip of the right atrium. The lower support is clamped in a femur clamp and the upper hook is suspended from the strain gauge lug. The strain gauge is raised until the resting tension on the tissue is 1 gram. The tissue is allowed to stabilize for about one hour with several buffer washings and tension adjustments before the addition of the test compounds.

3. Test Procedure

A control dose-response curve using cumulative, approximately tripling doses is obtained in all three running from 0.1 to 30.0 μM histamine (0.1, 0.3, 1.0, 3.0, etc.) In order to minimize volume changes when adding drugs to the bath, small volumes of concentrated solutions are used. It is convenient to make up a 0.5M solution and dilute it to give 50, 5 and 0.5 mM solutions.

Data recorded consists of the initial baseline rate and the stable plateau rate after each addition. Histamine is then washed out and the tissues are allowed to stabilize again near the initial baseline rate; this may take several rinses and 1 hr. The test compound is then added at the same cumulative doses and rates again recorded. If the compound behaves as an agonist and stimulates, then the dose is increased until the rate plateaus or the concentration is 1.0 mM. If, however, no agonistic activity is observed when the concentrations has reached 100 μM then its antagonistic activity is assessed by repeating the histamine curve without washing out the test compound. Reversibility of effect is assessed by attempting to wash out the test compound and/or histamine and repeat the histamine curve. Erratic or irregular beating or any other abnormal behavior at any time is noted. Calculations consist of the change in rate from base line and that change as a percentage of the maximum rate obtained in the initial control curve. The mean of those percentages (±SEM) is plotted as a function of agonist concentration (either histamine or test compound) to evaluate the type of response.

B. Lumen Perfused Rat Stomach—Effect on the Gastric Secretion

Male Sprague-Dawley rats weighing between 350 and 500 gm are housed individually according to standard animal husbandry procedures and are deprived of food twenty-four hours prior to testing. The rats are anesthetized by an intraperitoneal injection of 25% solution of urethane (0.5 to 0.7 ml/100 g of body weight). Once anesthetized, the trachea is exposed and cannulated with PE 100 tubing. The jugular vein is exposed and cannulated with PE 50 tubing bevelled at the tip. The abdomen is opened through a midline incision, and the esophagus is isolated excluding the vagus nerve. PE 190 tubing, with a flange on one end, is passed down the rat's mouth through the esophagus and into the stomach. The esophagus is tied off and the tubing checked to make sure that it is securely in the stomach. The duodenum is then identified and a small cut made about 1 cm below the pyloric sphincter. A piece of PE 320 tubing (flanged at one end) is inserted through the cut and into the stomach. It is secured firmly by tying a ligature around the pylorus. Using a 50 ml syringe, the stomach is flushed out with 0.4 mM NaOH through the esophageal tube until the perfusate emerging from the pyloric tube is clear. The animal is placed on a tilted table covered with a Gordon-Rupp water blanket Model 'K' to maintain the rat's body temperature at 30° C. The tube going into the esophagus is attached to a Sage Peristaltic Pump and 0.4 mN NaOH (pH 10.0) is perfused and collected in 30 ml beakers. The beakers are changed every 10 or 15 minutes and the pH of these samples are recorded. Once the pH has stabilized around 6.5–7.5, drugs that affect gastric secretion are given intravenously. The effectiveness of a compound is based on its ability to prevent a drop in pH initiated by a gastric stimulant, such as histamine. See, Ghosh, M. N. and Schild, H. O., *Brit. J. Pharmacol.*, 13: 54 (1958).

Compounds within the scope of Formula I have also been determined to exhibit anti-ulcer activity. The anti-ulcer properties of these compounds can be evaluated using an anti-ulcer assay in which aspirin or another nonsteroidal anti-inflammatory agent is used to induce gastric ulcers in the rat according to the following test procedure.

See, Corell, T., "Interaction of Salicylates and other Non-steroidal Anti-inflammatory Agents in Rats as Shown by Gastro-ulcerogenic and Anti-inflammatory Activities, and Plasma Concentrations", Acta. Pharmacology et. Toxicology, 45, 255–231 (1979).

Male Sprague-Dawley rats 140–170 g are housed according to standard animal husbandry procedures. The rats are fasted twenty-four hours prior to testing. On the test day, rats are divided into groups of 5 or 10, with one group serving as controls and receiving vehicle (for example, distilled water or a 0.1% Tween 80 solution). The test compounds, using logarithmic doses, are administered at a dose volume of 10 ml/kg. Thirty minutes post-drug, the rats are orally administered (10 ml/kg) aspirin or indomethacin suspended in 0.1% Tween 80 at a dose of 150.0 or 20.0 mg/kg, respectively. Four hours following indomethacin administration (five hours after aspirin administration) animals are sacrificed via cervical dislocation; their stomachs are removed, opened along the greater curvature, and gently rinsed and examined for lesions with a 10× magnifying glass; the following scale is employed:

| Grade | Description |
|---|---|
| 0 | No lesions |
| 1 | 5 lesions, all <2 mm |
| 2 | 5 lesions, at least 1 > 2 mm |
| 3 | 5–10 lesions, all <2 mm |
| 4 | 5–10 lesions, at least 1 > 2 mm |
| 5 | 10 lesions, all <2 mm |
| 6 | 10 lesions, at least 1 > 2 mm |
| 7 | Perforation |

The average ulcer severity (±S.E.) for each group of animals is calculated. The percent inhibition for each test compound is calculated as follows:

% inhibition =

$$\frac{\text{Mean value for control} - \text{Mean value for experimental}}{\text{Mean value for control}} \times 100$$

The compounds for Formula I have also been determined to exhibit cytoprotective activity.

The cytoprotective effectiveness of the compounds of Formula I is evaluated according to the following test procedure.

Male Sprague-Dawley rats 150-200 g are housed according to standard animal husbandry procedures. The rats are fasted twenty-four hours prior to testing. On the test day, rats are divided into groups of 6, with one group serving as controls and receiving vehicle (for example, distilled water or a 0.5% Methocel solution). The test compounds, using logarithmically spaced doses, are administered at a dose volume of 5 ml/kg. Ten minutes post-drug, the rats are orally administered 1 ml of absolute alcohol, 0.2N NaOH (1 ml) or 0.6N HCl (1 ml), regardless of body weight. One hour after administration animals are sacrificed by cervical dislocation, their stomachs are removed, opened along the greater curvature, rinsed under running tap water and examined for lesions with a 2×-10× magnifying glass.

The reduction of lesion count, lesion severity score and ulcer index as compared to similar measurements made in the controls was expressed as a percentage. Measurement of statistical significance of the results was done by standard methods.

The average ulcer severity ($\pm$S.E.) for each group of animals is calculated. The percent inhibition for each test compound is calculated as follows:

$$\% \text{ inhibition} = \frac{\text{Mean value for control} - \text{Mean value for experimental}}{\text{Mean value for control}} \times 100$$

The results of the anti-secretory, anti-ulcer and cytoprotective assays, detailed above, establish the anti-secretory activity, the $H_2$-receptor antagonist activity, the anti-ulcer activity, the cytoprotective activity, and the utility of the compounds of the present invention in the treatment of peptic ulcers in mammals, including humans. These compounds both aid in the healing of such ulcers and also prevent their formation.

A preferred class of $H_2$-antagonist compounds are compounds of Formulae I through V wherein $R_2$ and $R_3$ are other than hydrogen.

Another preferred class of compounds are orally active compounds of Formulae I through V wherein $R_7$ is thiadiazole monoxide and $R_3$ is other than hydrogen.

The most preferred $H_2$-antagonist compounds within the scope of Formula I exhibit $H_2$-antagonist activity comparable to or greater than the $H_2$-antagonist activity of Cimetidine, as measured by the guinea pig atria test. Examples of the most preferred $H_2$-antagonist compounds are listed in Table C below.

TABLE C

| Name | M.P. |
| --- | --- |
| 3-Amino-4-[3-[5-[1-(1-piperidinylmethyl)benzocyclobutenyloxy]propylamino]]-1,2,5-thiadiazole-1-oxide | 175-176° C. |
| 3-Amino-4-[3-[5-[1-methyl-1-(1-piperidinylmethyl)benzocyclobutenyloxy]propylamino]]-1,2,5-thiadiazole-1-oxide | 115-119° C. |
| 3-Amino-4-[3-[5-[trans-2-methyl-1-(1-piperidinylmethyl)benzocyclobutenyloxy]propylamino]]-1,2,5-thiadiazole-1-oxide.¼$H_2O$ | 125-127° C. |
| 3-Amino-4-[3-[5-[cis-2-methyl-1-(1-piperidinylmethyl)benzocyclobutenyloxy]propylamino]]-1,2,5-thiadiazole-1-oxide | 136-138° C. |
| 3-Amino-4-[3-[5-[1-allyl-1-(1-piperidinylmethyl)benzocyclobutenyloxy]propylamino]]-1,2,5-thiadiazole-1-oxide | 176-178° C. |
| 3-Amino-4-[3-[5-[1-dimethylaminomethyl-1-(1-piperidinylmethyl)benzocyclobutenyloxy]propylamino]]-1,2,5-thiadiazole-1-oxide | 183-185° C. |
| 3-Amino-5-[3-[5-[1-methyl-1-(1-piperidinylmethyl)benzocyclobutenyloxy]propylamino]]-1-methyl-1H—1,2,4-triazole | 67-69° C. |
| 3-Amino-5-[3-[5-[1-allyl-1-(1-piperidinylmethyl)benzocyclobutenyloxy]propylamino]]-1-methyl-1H—1,2,4-triazole | 89-90° C. |
| 3-Amino-5-[3-[5-[trans-2-methyl-1-(1-piperidinylmethyl)benzocyclobutenyloxy]propylamino]]-1-methyl-1H—1,2,4-triazole | 90-92° C. |
| 2-Amino-1-[3-[5-[1-methyl-1-(1-piperidinylmethyl)benzocyclobutenyloxy]propylamino]]-1-cyclobutene-3,4-dione | 225-228° C. |

In particular, the compounds according to Formulae I to V are useful: in the treatment and prevention of hyperacidity and gastrointestinal ulceration; for decreasing gastrointestinal acid secretion in mammals; and for enhancing the gastrointestinal resistance to gastrointestinal irritants in humans and other mammals.

For all these purposes, the compounds of this invention can be normally administered orally or parenterally. Oral administration is preferred.

The compounds according to the invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, for example, $H_1$-antagonists, or known antacids such as aluminum hydroxide, magnesium hydroxide, magnesium trisilicate, aluminum glycinate, or calcium carbonate. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, and made isotonic with sufficient saline or glucose.

The dosage regimen in carrying out the methods of this invention is that which ensures maximum therapeutic response until improvement is obtained and thereafter the minimum effective level which gives relief. Thus, in general, the dosages are those that are therapeutically effective in the treatment of gastrointestinal disease conditions or symptoms, such as duodenal and peptic ulcer. In general, the dose can be between about 0.1 mg/kg and 100 mg/kg (preferably in the range of 1 to 20 mg/kg), bearing in mind, of course, that in selecting the appropriate dosage in any specific case, consideration must be given to the patient's weight, general health, age, and other factors which may influence response to the drug. The daily dose can range from 1 to 4 times a day.

We claim:

1. A compound of the formula

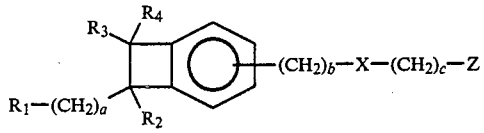

wherein:
a is 1 or 2;
b is 0 or 1;
c is 2, 3 or 4;
X is oxygen, sulfur,

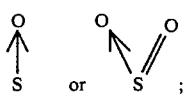

Z is —NHR$_7$;
R$_1$ is —NR$_5$R$_6$;
R$_2$, R$_3$ and R$_4$ are each independently hydrogen, lower alkyl, allyl, arylloweralkyl, loweralkoxycarbonyl or lower alkyl substituted by hydroxy, loweralkoxycarbonyl or NR$_5$R$_6$;
R$_5$ and R$_6$ are each independently H or alkyl, or both together with the nitrogen to which they are attached form a 5, 6 or 7-membered ring which may include one to three additional hetero atoms of N, O or S;
R$_7$ is selected from the group consisting of

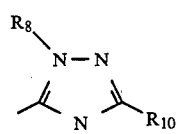

R$_8$ is H or lower alkyl;
R$_{10}$ is hydrogen, lower alkyl, lower alkenyl, aryl, arloweralkyl, hydroxyloweralkyl, acyloxyloweralkyl, loweralkoxyloweralkyl, aryloxyalkyl, aroyloxyalkyl, aralkyloxyalkyl, aminoalkyl, alkylaminoalkyl, dialkylaminoalkyl, hydroxy, alkoxy, alkylthio, halogen or NR$_{11}$R$_{12}$, where:
R$_{11}$ is hydrogen, lower alkyl, lower alkenyl or arloweralkyl; and
R$_{12}$ is hydrogen, COR$_{13}$, SO$_2$R$_{14}$ or

R$_{13}$ is hydrogen, lower alkyl, aryl, arloweralkyl, loweralkoxy, heteroaryl, or monocyclic heteroarylalkyl;
R$_{14}$ is loweralkyl or aryl;
R$_{15}$ is hydrogen, lower alkyl, cycloloweralkyl, aryl or lower aralkyl;
wherein the term aryl is phenyl or substituted phenyl
or a pharmaceutically acceptable salt thereof.

2. A compound according to claim 1 wherein a is 1.

3. A compound according to claim 2 wherein:
b is 0;
c is oxygen;
Z is NHR$_7$;
R$_1$ is NR$_5$R$_6$; and
R$_3$ and R$_4$ are hydrogen.

4. A compound of the formula

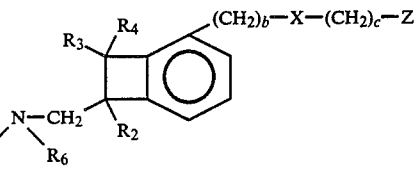

wherein:
b is 0 or 1;
c is 2, 3 or 4;
X is oxygen or sulfur;
Z is —NHR$_7$;
R$_2$, R$_3$, and R$_4$ are each independently hydrogen, lower alkyl, allyl, arylloweralkyl, loweralkoxycarbonyl or lower alkyl substituted by hydroxy, loweralkoxycarbonyl or NR$_5$R$_6$;
R$_5$ and R$_6$ are each independently H or alkyl, or both together with the nitrogen to which they are attached form a 5, 6 or 7-membered ring which may include one to three additional hetero atoms of N, O or S;
R$_7$ is selected from the group consisting of

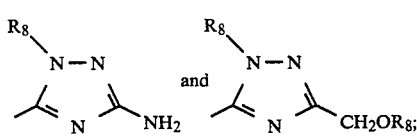

R$_8$ is H or lower alkyl;
or a pharmaceutically acceptable salt thereof.

5. A compound of the formula

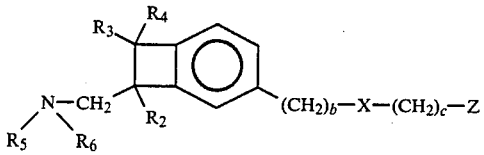

wherein:
 b is 0 or 1;
 c is 2, 3 or 4;
 X is oxygen or sulfur;
 Z is —$NHR_7$;
 $R_2$, $R_3$, and $R_4$ are each independently hydrogen, lower alkyl, allyl, arylloweralkyl, loweralkoxycarbonyl or lower alkyl substituted by hydroxy, loweralkoxycarbonyl or $NR_5R_6$;
 $R_5$ and $R_6$ are each independently H or alkyl, or both together with the nitrogen to which they are attached form a 5, 6 or 7-membered ring which may include one to three additional hetero atoms of N, O or S;
 $R_7$ is selected from the group consisting of

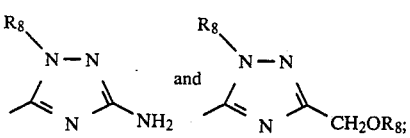

$R_8$ is H or lower alkyl;
or a pharmaceutically acceptable salt thereof.

6. A compound according to claim 4 wherein:
 b is 0,
 X is oxygen;
 $R_1$ is $NR_5R_6$; and
 $R_3$ is hydrogen.

7. A compound according to claim 5 wherein:
 b is 0;
 X is oxygen;
 $R_1$ is $NR_5R_6$; and
 $R_3$ is hydrogen.

8. A compound of the formula

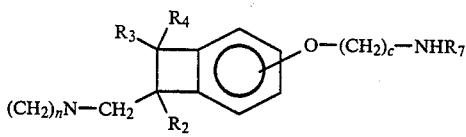

wherein:
 c is 2, 3 or 4;
 n is 4, 5 or 6;
 $R_2$, $R_3$, and $R_4$ are each independently hydrogen, lower alkyl, allyl, arylloweralkyl, loweralkoxycarbonyl or lower alkyl substituted by hydroxy, loweralkoxycarbonyl or $NR_5R_6$;
 $R_5$ and $R_6$ are each independently H or alkyl, or both together with the nitrogen to which they are attached form a 5, 6 or 7-membered ring which may include one to three additional hetero atoms of N, O or S;
 $R_7$ is selected from the group consisting of

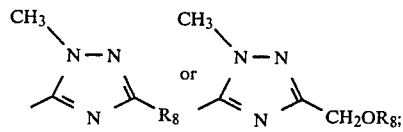

$R_8$ is H or lower alkyl;
or a pharmaceutically acceptable salt thereof.

9. A compound according to claim 8 wherein:
 c is 3; and
 $R_2$, $R_3$ and $R_4$ are hydrogen.

10. A compound according to claim 8 wherein:
 c is 3; and
 $R_3$ and $R_4$ are hydrogen.

11. A compound according to claim 8 wherein:
 c is 3; and
 $R_2$ is hydrogen.

12. A compound according to claim 8 wherein:
 c is 3; and
 $R_2$ and $R_3$ are hydrogen.

13. A compound according to claim 12 wherein the $R_4$ substituent is cis relative to the $(CH_2)_nN—CH_2$—substituent.

14. A compound according to claim 13 wherein the $R_4$ substituent is trans relative to the $(CH_2)_nN—CH_2$—substituent.

15. A compound according to claim 1 which is 3-amino-5-[3-[3'-[1-[1-piperidinylmethyl]benzocyclobutenyloxy]propylamino]]-1-methyl-1H-1,2,4-triazole, or a pharmaceutically acceptable salt thereof.

16. A compound according to claim 1 which is 3-amino-5-[3-[5-[1-methyl-1-(1-piperidinylmethyl)benzocyclobutenyloxy]propylamino]]-1-methyl-1H-1,2,4-triazole, or a pharmaceutically acceptable salt thereof.

17. A compound according to claim 1 which is 3-amino-5-[3-[5-[1-allyl-1-(1-piperidinylmethyl)benzocyclobutenyloxy]propylamino]]-1-methyl-1H-1,2,4-triazole, or a pharmaceutically acceptable salt thereof.

18. A compound according to claim 1 which is 3-amino-5-[3-[5-[trans-2-methyl-1-(1-piperidinylmethyl)benzocyclobutenyloxy]propylamino]]-1-methyl-1H-1,2,4-triazole, or a pharmaceutically acceptable salt thereof.

19. A method for decreasing acid secretion in the gastrointestinal tract of mammals by administering thereto an anti-secretory effective amount of a compound according to claim 1.

20. A method for the treatment of gastrointestinal hyperacidity and ulceration in a mammal comprising administering thereto an effective amount of a compound according to claim 1.

21. A method for enhancing the gastrointestinal resistance to gastrointestinal irritants in humans and mammals comprising administering thereto an effective cytoprotective amount of a compound of the formula according to claim 1.

22. A pharmaceutical composition wherein the active ingredient is a compound according to claim 1 in admixture with a pharmaceutical carrier.

* * * * *